(12) United States Patent
Walsh

(10) Patent No.: US 7,766,814 B2
(45) Date of Patent: Aug. 3, 2010

(54) VESSEL OR SAC WALL TREATMENT AND A CARDIAC ASSIST DEVICE

(76) Inventor: Peter William Walsh, 21 Reedan Street, Everton Park, Queensland 4053 (AU)

( * ) Notice: Subject to any disclaimer, the term of this patent is extended or adjusted under 35 U.S.C. 154(b) by 294 days.

(21) Appl. No.: 10/584,807

(22) PCT Filed: Mar. 2, 2005

(86) PCT No.: PCT/AU2005/000299

§ 371 (c)(1),
(2), (4) Date: Jun. 28, 2006

(87) PCT Pub. No.: WO2005/084730

PCT Pub. Date: Sep. 15, 2005

(65) Prior Publication Data

US 2008/0194905 A1    Aug. 14, 2008

(30) Foreign Application Priority Data

Mar. 2, 2004 (AU) ............... 2004901070
Mar. 2, 2004 (AU) ............... 2004901071

(51) Int. Cl.
*A61N 2/04* (2006.01)
(52) U.S. Cl. .......................... 600/17; 600/16
(58) Field of Classification Search ............. 600/16–18, 600/31; 623/3.17
See application file for complete search history.

(56) References Cited

U.S. PATENT DOCUMENTS

| | | | | |
|---|---|---|---|---|
| 3,974,825 A | * | 8/1976 | Normann | 600/17 |
| 4,256,094 A | * | 3/1981 | Kapp et al. | 601/152 |
| 4,813,952 A | * | 3/1989 | Khalafalla | 623/3.12 |
| 4,938,766 A | * | 7/1990 | Jarvik | 623/3.17 |
| 4,979,936 A | * | 12/1990 | Stephenson et al. | 600/16 |
| 5,409,444 A | | 4/1995 | Kensey et al. | |
| 6,030,335 A | * | 2/2000 | Franchi | 600/16 |
| 6,030,336 A | * | 2/2000 | Franchi | 600/18 |
| 6,045,496 A | * | 4/2000 | Pacella et al. | 600/16 |
| 6,050,932 A | * | 4/2000 | Franchi | 600/16 |
| 6,402,779 B1 | | 6/2002 | Colone et al. | |
| 6,494,906 B1 | | 12/2002 | Owens | |
| 6,524,334 B1 | | 2/2003 | Thompson | |
| 6,572,649 B2 | | 6/2003 | Berry et al. | |
| 6,579,223 B2 | * | 6/2003 | Palmer | 600/16 |
| 6,605,107 B1 | | 8/2003 | Klein | |
| 6,626,939 B1 | | 9/2003 | Burnside et al. | |
| 6,673,103 B1 | | 1/2004 | Golds et al. | |
| 6,808,484 B1 | * | 10/2004 | Peters et al. | 600/18 |
| 6,827,682 B2 | * | 12/2004 | Bugge et al. | 600/16 |
| 7,347,811 B2 | * | 3/2008 | Peters et al. | 600/18 |
| 2003/0093145 A1 | | 5/2003 | Lawrence-Brown et al. | |
| 2003/0125797 A1 | | 7/2003 | Chobotov et al. | |
| 2003/0233023 A1 | * | 12/2003 | Khaghani et al. | 600/18 |

(Continued)

FOREIGN PATENT DOCUMENTS

BG    109148    5/2005

(Continued)

*Primary Examiner*—Carl H Layno
*Assistant Examiner*—Luther G Behringer
(74) *Attorney, Agent, or Firm*—Baker & Daniels LLP

(57) ABSTRACT

The present invention provides a device and method of treating a vessel in a human or animal body.

43 Claims, 13 Drawing Sheets

U.S. PATENT DOCUMENTS

| | | |
|---|---|---|
| 2004/0097784 A1 | 5/2004 | Peters et al. |
| 2004/0102838 A1 | 5/2004 | Killion et al. |
| 2004/0106971 A1 | 6/2004 | Schwartz et al. |
| 2004/0133260 A1 | 7/2004 | Schwartz et al. |
| 2004/0143319 A1 | 7/2004 | Schwartz et al. |
| 2004/0254625 A1 | 12/2004 | Stephens et al. |
| 2005/0027346 A1 | 2/2005 | Arkusz et al. |

FOREIGN PATENT DOCUMENTS

| | | | |
|---|---|---|---|
| EP | 0329765 B1 | 8/1989 | |
| WO | WO 89/01765 | 3/1989 | |
| WO | WO 96/07371 | 3/1996 | |
| WO | WO 00/76288 | * 12/2000 | |
| WO | WO 03/011365 | 2/2003 | |
| WO | WO 2004/019819 | 3/2004 | |
| WO | WO 2004/026112 | 4/2004 | |
| WO | WO 2004/056274 | 7/2004 | |
| WO | WO 2005/084730 | * 9/2005 | |

* cited by examiner

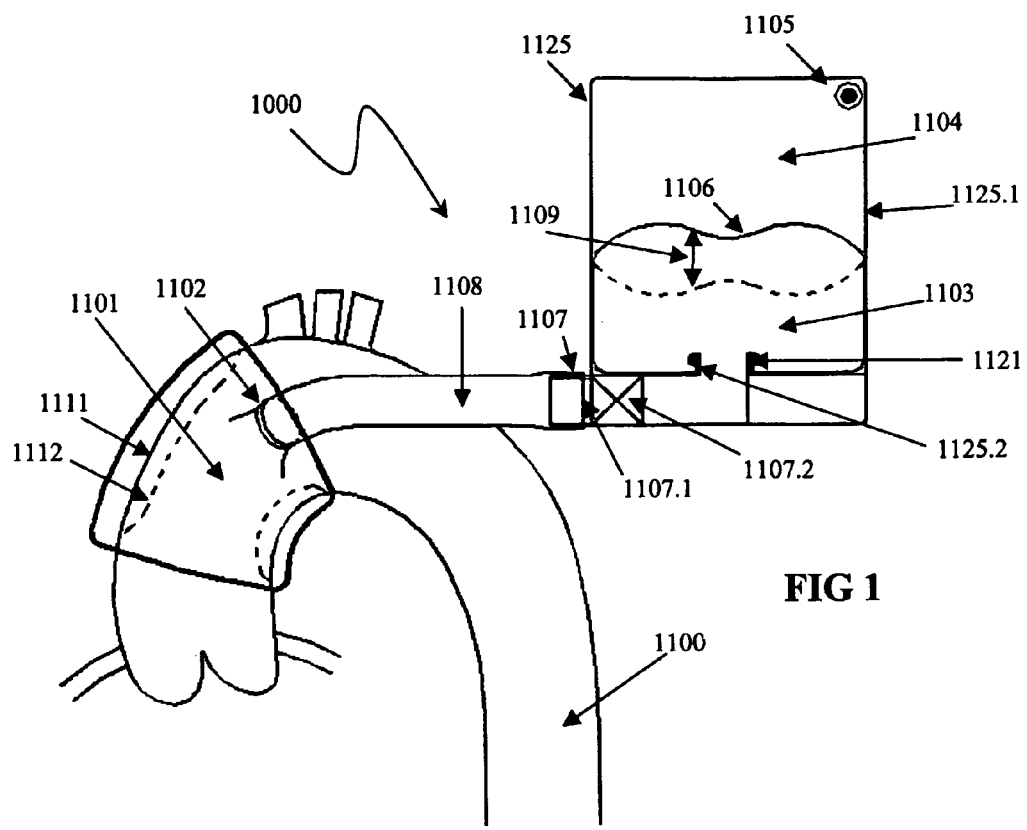
FIG 1
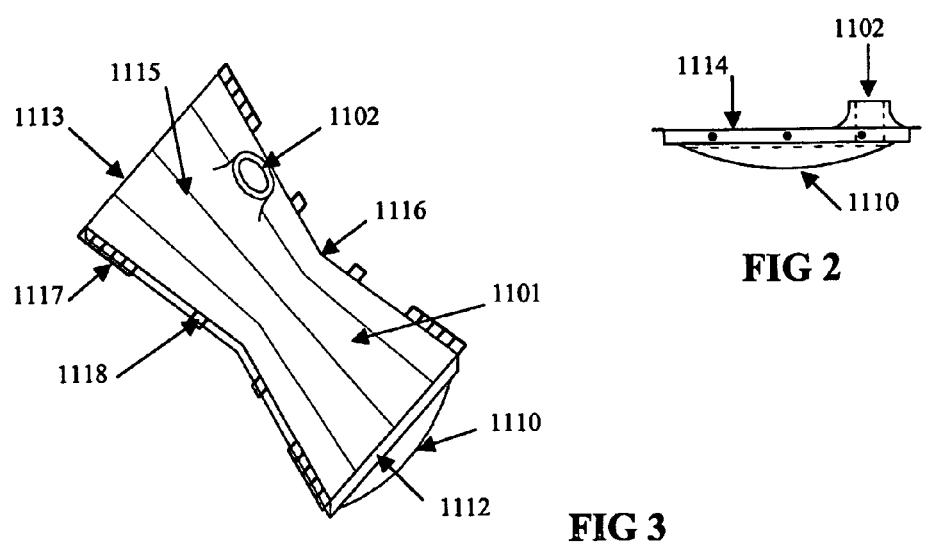
FIG 2
FIG 3

STENT  0.2 - 0.3 mm central struts
0.3 - 1.0 mm end struts

POLYURETHANE TUBE
0.5 - 1.0mm thickness

VESSEL OR SAC WALL TREATMENT AND A CARDIAC ASSIST DEVICE

CROSS-REFERENCE TO RELATED APPLICATIONS

This application is a nationalization of PCT Patent Application Serial No. PCT/AU2005/000299, filed Mar. 2, 2005, which claims the benefit of Serial No. 2004901071, filed Mar. 2, 2004 and Serial No. 2004901070, filed Mar. 2, 2004, the disclosures of which are expressly incorporated herein by reference.

FIELD OF THE INVENTION

The present invention relates to tubular wall compliance and load bearing devices and methods for their deployment within human and or animal bodies, so as to change or modify the compliance or the load bearing capacity of a tubular or sac wall section.

When applied to the cardiovascular system, these inventions serve to boost the secondary heart pump action of the heart, by dampening the time dependent blood pressure profile during systole, and enhancing the time dependent blood pressure profile during diastole, thereby reducing heart load and improving aortic and coronary artery blood flow.

BACKGROUND OF THE INVENTION

Heart failure is the fastest growing cardiovascular disorder. Incidence is rising at a rate of approximately 2% to 5% in people over 65 years of age, and 10% in people over 75 years of age.

Heart failure is a leading cause of hospital admissions and re-admissions in Americans older than 65 years of age.

Hypertension is a common condition prior to heart failure. In a recent study; 91% of people who developed heart failure had previous hypertension, of which 42% had systolic dysfunction and 58% had diastolic dysfunction.

Aortic stiffening, due to elastin degradation and other forms of stiffening, such as that caused by atherosclerosis, which is stiffening due to the presence and build up of plaques, are a cause of hypertension. The aorta stiffens and dilates with age increasing: the load on the heart; pressure in left ventricle; aortic pressure at the time of peak aortic flow, and pulse wave velocity in the aorta and early wave reflection thus increasing pressure in late systole.

Data shows that systolic blood pressure continues to rise with age and diastolic pressure remains constant after approximately 50 years of age, giving an increase in pulse pressure after 50 years of age.

As the aorta stiffens, the arterial system suffers from a lack of compliance, leading to hypertension (FIGS. 8 and 9). Therefore aortic stiffening appears to be a factor leading to heart failure.

Aortic compliance is fundamental to effective cardiovascular dynamics. Lack of aortic compliance leads to increased heart loading during systole and poor coronary artery perfusion during diastole due to a lack of vessel recoil. Decreases in aortic compliance occur with age as a result of stiffening in the aortic wall. Approximately 80% of arterial compliance is in the ascending aorta and aortic arch sections. This expansion during systole and contraction/recoil during diastole of the ascending aorta and arch, is referred to as the secondary heart pump; an action that decays with age and disease.

Stiffness of the aortic wall can be defined using various measures, and is commonly expressed as the pressure-strain elastic modulus, $E_P$:

$$E_P = D_{dia} \times (D_{sys} - D_{dia})/(P_{sys} - P_{dia})$$

Where $D_{sys}$ and $D_{dia}$ and the diameter of the vessel in systole and diastole respectively, and $P_{sys}$ and $P_{dia}$ are the pressure within the vessel at systole and diastole respectively.

Aortic stiffening is generally associated with vessel dilation. Previous solutions for addressing heart failure include:
(a) medications which have limited benefits and generally high costs associated with them:
(b) intra-aortic balloons which are only a temporary solution:
(c) ventricular assist devices, extraluminal and intraluminal compression devices and pumps, which require power sources thereby increasing complexity of implanting, increase expense and have higher risk to the patient, and
(d) heart transplants which are limited by availability, high cost and high risk.

The applicant does not concede that the prior art discussed in the specification forms part of the common general knowledge in the art at the priority date of this application.

SUMMARY OF THE INVENTION

The present invention provides a method of treating a vessel in a human or animal body, said method including the steps of preparing a patient; identifying a site in said vessel requiring treatment, positioning an implantable device against a portion of tubular or sac wall of said vessel at said site, whereby load applied to said vessel is borne by said wall and said device, said vessel being assisted by said device when said wall and said device acts upon said load, said device including an energy storage means which is charged with a pressure or energy charge by means of said load being applied to said vessel.

The present invention also provides a method of treating a vessel in a human or animal body, said method including the steps of preparing a patient; identifying a site in said vessel requiring treatment; replacing all or a portion of said vessel requiring treatment with an implantable device, whereby load applied to the vessel is borne by said device, said vessel being assisted by said device when said device acts upon said load, said device including an energy storage means which is charged with a pressure or energy charge by means of said load being applied to said vessel.

The pressure or energy charge can be an energy charge which is at least in part produced by elastic deformation of said device.

Operation of said device can result in a system containing said vessel operating in a less stiff and or more compliant manner than would have been present from said portion of said wall at said site as untreated.

The energy storage means releases said pressure or energy charge to enable said device to assist said wall when said wall acts upon said load.

The device can include at least one elastomeric component, said elastomeric component being adapted to release energy to assist said vessel.

The device or said energy storage means releases said pressure or energy charge in response to unloading of said vessel.

The method can include positioning a cuff, which is a part of said device, around said wall.

The energy storage means can be a windkessel.

The energy storage means can include a compressible media chamber which when compressed stores said pressure or energy charge.

The compliance of the device can be modified at the time of implant by inflation.

Compliance can be modified by inflation with one, or a combination of more than one, of the following media: a bio-compatible fluid; liquid silicone; liquid saline; a liquid containing a contrast agent (x-ray viewable); a gel solution that expands with temperature to a final operating volume at 37° degrees Celsius; uncured or liquid polymer which is thermosetting, at 37° C. or via activation by light or heat; a heat activated gel; elastin; collagen; elastin and collagen in combination; air, a polymer that cures or thermosets after injecting gas, carbon dioxide, helium, or air or other compressible media.

The vessel can be a blood vessel.

The load applied to said vessel being borne by said wall and said device can be a systole phase of a cardiovascular system.

When said wall and said device acts upon said load it can be a diastole phase of a cardiovascular system.

The device can be positioned externally onto said vessel or the device can be positioned within said vessel or the device can be positioned between cut ends of said vessel to replace said site.

The present invention further provides a treatment or assistance device for operating in or with a tubular or sac wall of a vessel in a human or animal body, said device including a changeable volume portion which is adapted to interact with said vessel so as to modify the volume of said vessel; and an energy storage means functioning with said changeable volume portion whereby a decrease in the volume of said changeable volume portion creates a pressure or energy charge in said energy storage means, said pressure or energy charge being able to be subsequently released to cause said changeable volume portion to increase in volume.

The changeable volume portion can be a cuff member which includes an inflatable portion, said cuff member and said inflatable portion being able to be positioned around said vessel.

The energy storage means can be a pressure storage means such as a windkessel. The can pressure storage means include at least one valve, or at least one respective valve, to control the rate of charging and the rate of discharging of said pressure charge.

The changeable volume portion can be constructed at least in part from an elastomeric material, said elastomeric material being said energy storage means.

The changeable volume portion can be a graft or a stent graft or a part thereof and said energy storage means is an elastomeric material which forms said graft, or said stent, or said part.

The changeable volume portion and said energy storage means can be are primed with a threshold or reference pressure.

The media with which the changeable volume portion can be primed with one or more of the following media: a bio-compatible fluid; liquid silicone; liquid saline; a liquid containing a contrast agent which is x-ray viewable; a gel or other solution that expands with temperature to a final operating volume at 37° degrees Celsius; elastin; collagen; elastin and collagen in combination; air; carbon dioxide; helium, or a gas.

The energy storage means can include a compressible fluid chamber.

Media with which said energy storage means can be primed is one or more of the following compressible media: air, carbon dioxide, helium, or gas, or other compressible media.

The changeable volume portion can include a generally inextensible outer portion whereby any change of volume is confined to being within the volume defined by said outer portion.

The device can be adapted, at least in part, to be implanted into a human or animal body, The changeable volume portion and said pressure charging means can implanted in said human or animal body.

The changeable volume portion can be implanted in said human or animal body while said energy storage means, if separate from said changeable volume portion, can be located outside of said human or animal body.

The changeable volume portion can be joined to ends of said vessel.

The changeable volume portion can be attached externally to said vessel.

The changeable volume portion can be attached in the vessel.

The device can be used to treat or assist a blood carrying vessel.

The device can be used to repair the compliance of a portion of said vessel.

The device can be used to modify the systolic and diastolic characteristics of said vessel to thereby improve cardiovascular performance.

BRIEF DESCRIPTION OF THE DRAWINGS

An embodiment of the present invention will now be described, by way of example only, with reference to the accompanying drawings, in which:

FIG. 1 is a schematic of a device having an inflatable cuff located on an ascending aorta and an associated windkessel;

FIG. 2 is an end view of the cuff of FIG. 1 when not deployed;

FIG. 3 illustrates a perspective view of the cuff of FIG. 2;

DETAILED DESCRIPTION OF THE EMBODIMENT

Figure 10:
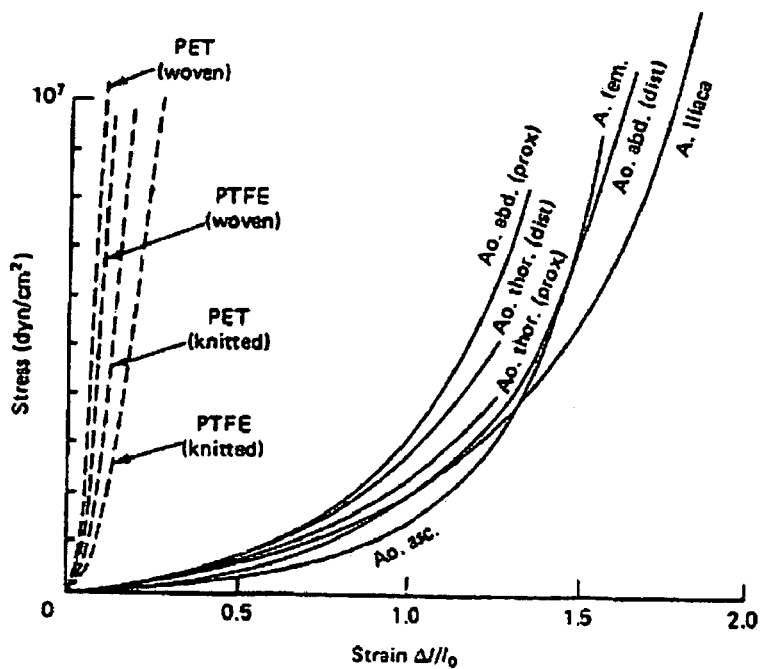
FIG. 10 is a stress-strain relationship graph for typically used graft materials as well as various blood vessels of the human body.

Illustrated in FIG. 10 is a stress-strain relationship graph indicating typically used graft materials and a comparison against normal blood vessels of the human body. The values plotted for the materials clearly indicate that they are not compliant enough for reducing stiffness in vessel wall applications. Age or otherwise stiffened vessels have a stress-strain relationship equivalent to PET and PTFE.

Figure 8:
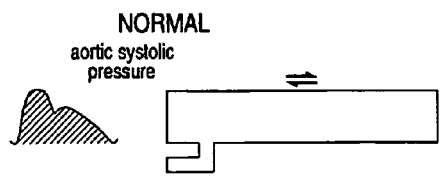
FIG. 8 is a schematic of a normal aorta with a corresponding pressure graph.
Figure 9:
FIG. 9 is a schematic of an aged aorta with a corresponding pressure graph.

The increased stiffness of aged vessels, results in a greater aortic systolic pressure and a reduced pressure decay during diastole, than compared to younger vessels, as indicated in FIGS. 8 and 9.

Aneurysm treatment using stent grafts suffer from leakage, migration and can leave a significant unfilled zone between the aneurysms sac and the stent graft, and additionally they reduce arterial compliance by use of non-compliant materials shown to increase systolic pressure and lower diastolic discharge much like an aged stiffened vessel.

It is to these difficulties that the following described embodiments are addressed in order to attempt to alleviate or ameliorate one or more of these difficulties.

Extraluminal Cuff 1101 with Inflatable Cuff Balloon 1110

Illustrated in FIG. 1 is a device 1000 deployed on a vessel 1100. The device 1000 includes a flexible cuff 1101 which is positioned about the vessel 1100, which in the present instance is an ascending aorta, but can be any aortic vessel, or other vessel, or body conduit The cuff 1101 includes an inflatable portion or bag referred to as the cuff balloon 1110.

Illustrated in FIGS. 1, 2 and 3, the cuff 1101 includes a port 1102 having a septum seal (not illustrated), allowing the cuff balloon 1101 to be air or gas filled at the time of the surgical implantation, or adjusted after implantation by means external to the body, such as via a syringe and needle access through the chest wall. The cuff 1101 can be implanted thorascopically.

The cuff 1101 is flexible along its width and length and is constructed so that the outer thicker layer 1114 does not circumferentially distend when the cuff balloon 1110 is pressurised, thus allowing an efficient coupling between the cuff balloon 1110 and the outer wall of the vessel 1100.

The cuff 1101 can include reinforcing fibres or wire struts 1115 which are affixed to or are imbedded in, the outer layer 1114 in order to maximise transfer of loads between the cuff balloon 1110 and the wall of the vessel 1100. The cuff 1101 is flexible enough to follow the shape of the outer wall of the vessel 1100 when applied. Once the cuff 1101 is positioned around the outer wall of the vessel 1100, the opposed ends 1112 and 1113 will be adjacent to each other, where they are overlapped and locked together via any appropriate means such as staples, pegs, suturing, gluing etc, so that the cuff 1101 can remain in place surrounding the vessel 1100.

The reinforcing fibres or wire struts 1115, allow the cuff 1101 to maintain its flexibility so as to be positioned around the outside of the wall of the vessel 1100, but also allow the outer surfaces of the cuff 1 101 to be relatively inextensible, whereby the change in volume of the cuff balloon 1110 is transmitted to distend or expand the wall of the vessel 1100.

As can be seen in FIG. 3, when the cuff 1101 is laid our flat, before forming an endless ring as described above, the cuff 1101 has a converging then diverging shape as it extends from one end 1112 to the opposing end 1113. The converging diverging shape produces a centre region 1116 of reduced width, which allows the cuff 1101 to properly sit on a vessel 1100, such as the ascending aorta, which has a radius of curvature associated therewith. The reduced width engages the smaller radius of curvature, while the ends 1112 and 1113, end up being secured along or adjacent to the larger radius of curvature of the vessel 1100. This converging diverging shape could be used on vessels which have no curvature, but in the case of vessels not having curvature, a cuff 1101 having straight or parallel sides may be preferred.

The cuff balloon 1110, in the vicinity of a cuff end is pushed flat by the other cuff end, depending upon which end 1112 or 1113 is overlying and underlying. The ends 1112 and 1113 can be fixed together temporarily by pegs that can be pre-loaded into the binding holes 1117 on the overlying cuff end, and once the diameter is adjusted on implantation, the overlying and underlying cuff ends 1112 and 1113 are locked into place by suturing, clips, permanent locking pegs, or wire or other means. The cuff 1101 can also have binding holes along the cuff edge 1118 that allow it to be sutured to the adventitia of the vessel 1100.

The cuff 1101 is intended to sit gently against and around the outer wall of the vessel with the cuff balloon 1110 reducing the vessel diameter by 5% to 15% at a threshold cuff inflation pressure (discussed in the next section). The reduction can be greater depending on the conditions of the patients and the properties of the vessel wall.

The cuff 1101 can be made of a polymeric material such as polyurethane, silicone, a combination of polyurethane and silicone, or other polymeric material, or fibre reinforced biocompatible polymeric materials. The cuff balloon 1110 can be made of flexible polyurethane, silicone, a combination of polyurethane and silicone, or other polymeric material, or elastomeric polyurethane, silicone, a combination of polyurethane and silicone, or other polymeric materials.

Extraluminal Cuff with Integral Energy Storage System

The extraluminal cuff 1101 can be used with a discrete energy storage system such as one that will store an energy or pressure charge as described below. Alternatively the extraluminal cuff 1101 can be used without a discrete energy storage system whereby cuff 1101 and the cuff balloon 1110 act as an integral energy storage system. In this case the balloon cuff 1101 can be filled with a compressible medium such as air or other gas or other compressible media so that the cuff balloon 1110 can absorb an energy or pressure charge when the vessel is in the systolic phase of a cardiovascular system. The volume of the cuff balloon 1110 can be increased for use when in such a stand alone mode to allow an increase in compliance when filled with a compressible medium.

Once the cuff 1101 has been deployed onto a vessel 1100 it is pressurised with gas to a threshold or reference pressure below systolic pressure. Once the internal blood pressure rises above the threshold (in systole), further compression of the gas in the cuff balloon 1110 results, reducing the volume of the cuff balloon 1110 thereby allowing the distension of the underlying vessel 1100 to the position indicated by the unbroken line 1111 of FIG. 1. When the vessel blood pressure decreases to below the threshold (in diastole), the compressed gas in the cuff balloon 1110 expands thereby increasing the volume of the-cuff balloon 1110 and contracting the underlying vessel 1100 to the position as indicated by the dotted lines 1112 in FIG. 1.

The threshold pressure or reference pressure can be the mean blood pressure of a healthy adult, which is around 100 mmHg, but can be higher for severe hypertensive patients, or lower for end-stage heart failure patients with hypotension, or can vary depending on the properties of the vessel section being treated.

The coupling of the cuff balloon 1110 and vessel 1100 offloads the vessel wall allowing vessel expansion (time dependent systolic pressure dampening), and vessel contraction (boost in time dependent diastolic pressure discharging) via the charge and discharge of the cuff balloon 1110, thereby restoring the secondary heart pump in the hypertensive, the aged stiffened and diseased stiffened vessel patients, and congestive heart failure patients, and when adjusted the hypotensive patient group such as those experiencing end stage heart failure.

The cuff 1101 as described above, allows the vessel 1100 to expand and contract more naturally by reducing the vessels stress-strain profile or pressure strain elastic modulus $E_P$, which is likely to avoid vessel atrophy, a problem with prior art technology which over compresses and stresses and or compacts the elastin structure in the vessel wall, causing smooth muscle cell apoptosis, and further stiffening the vessel wall.

Extraluminal Cuff and Discrete Energy Storage System-Windkessel

As is illustrated in FIG. 1, the device 1000 includes, in addition to the cuff 1101 a connector tube 1108 which provides fluid communication between the port 1102 of the cuff 1101 and a pressure operated energy storage system, which in this case is a windkessel 1125. The windkessel 1125 includes a compressible gas chamber 1104 (air or other gas could be utilised) which is pressurised to a threshold or reference pressure via a needle septum port 1105 at time of implanting, or after implanting by external access with a needle through the chest.

Inside the windkessel is a flexible diaphragm, wall, bag or balloon 1106 which seals off the compressible gas chamber 1104. The underside of the balloon 1106 includes a windkessel reservoir 1103, being of sufficient volume to allow the transfer of fluid to and from the cuff balloon 1110 in response to blood pressure.

The windkessel balloon 1106 can be made of a polyurethane, silicone or polyurethane silicone mix or other polymeric material or any biocompatible polymer or fibre reinforced polymer. The windkessel compressible gas chamber 1104 is formed in the windkessel housing 1125.1 which is sealed by the balloon 106 when it is attached to a spigot 1125.2 in the base of the housing 1125.1, using a connector and seal 1121. The windkessel housing can be made of stainless steel or other inflexible biocompatible material.

The outside of the windkessel 1125 includes a port 1107.1 around which is formed an external connector 1107 so that an end of the tube 1108 can connect to the windkessel 1125. The port 1107.1 can be controlled to be open or closed or there between by means of a valve 107.2.

The windkessel 1125 is connected via connector 1107 and connecting tube 1108 to the cuff 1101. The tube 1108 and cuff 1101 are filled with fluid to a predetermined volume (which is expected to be in the range of 25 ml to 100 ml but could be 2.5 ml to 150 ml) with the balloon 1106 being provided with sufficient room to move inside the windkessel 1125 over its range of movement, generally indicated by the arrow 1109. The connector tube 1108 can be integrally moulded or formed with the cuff 1101 or is undetachably secured or attached to the port 1102 of the cuff 1101, after manufacture.

Operation of the windkessel 1125 is similar to that described above for the gas filled cuff 1101, with a discrete energy storage system used with the cuff balloon 1110, the cuff balloon 1110 filled with an incompressible fluid (but could be a gas in certain circumstances) where incompressible fluid transfer occurs between the cuff balloon 1110 and the windkessel reservoir 1103, and visa versa, during operation. When the internal blood pressure rises above the pressure in the windkessel's compressible gas chamber 1104, fluid is pushed from the cuff balloon 1110 to the windkessel reservoir 1103 which allows the distension of the vessel 1100 to the position illustrated by the unbroken line 1111, thereby increasing the pressure in the windkessel compressible gas chamber 1104 during systole (thereby charging up the windkessel with a pressure or energy charge). The distension of the vessel and compression of gas in the windkessel's compressible gas chamber 1104, results in the dampening of the time dependent systolic pressure profile.

During diastole, as the internal blood pressure deceases below the pressure in the windkessel compressible gas chamber 1104, the compressible gas chamber 1104 acts on the balloon 1106 to transfer fluid from the windkessel reservoir 1103 to the cuff balloon 1110, thereby contracting the vessel 1100 to the position indicated by broken lines 1112, thus boosting aortic pressure in counter-pulsation to the heart, thereby boosting coronary artery and aortic blood flow.

The dampening of the pressure profile during systole and discharge of pressure during diastole, reduces the pulse pressure and increases circulation efficiency. Thus the charging and discharging of the windkessel 1125 via an aortic coupling enhances the secondary heart pump action.

The cuff balloon 1110, windkessel reservoir 1103 and connection tube 1108 would be filled with an incompressible fluid such as a liquid like water, saline, oil, liquid silicone, or silicone oil. Further, the windkessel's compressible gas chamber 1104, would be best filled with a compressible gas, such as carbon dioxide, helium, air, or other gas, but could also be filled with incompressible fluids such as water, saline, oil or other fluids or gases or combinations as required.

The valve 1107.2 is an optional component. However, if it is used it can be adjusted via a surgical screwdriver or other instrument to adjust the charge and discharge rates of the pressure or energy charge going into or coming out from the windkessel 1125. Separate charge and discharge valves could also be used to allow independent charge and discharge rates by switching the fluid path between each valve with the use of a solenoid switch and battery, with a means of controlling the switching gated to the beating heart with a pressure and or ECG probe and appropriate control electronics.

For safety, the windkessel system can include pressure probes that monitor the reservoir and gas chamber state. An electronic sensing circuit with an audible or vibrating alarm can be activated in the event of a cuff or Windkessel malfunction or failure.

The electronic instrumentation mentioned can be simple and of low power consumption so as to be powered by a long life battery over an extensive period.

The windkessel 1125 can be sub-cutaneously implanted over the rib cage, and fixed by tissues or otherwise adhered to the ribs, with the connector tube 1108 running under and or between the ribs to the cuff 1101, or at another suitable location within the chest wall. Alternatively the windkessel 1125 can be secured to the chest wall outside of the body and attached to the cuff 1101 by a connecting tube 1108, by means of a transcutaneous connector through the skin into the chest.

The placement of the cuff 1101 and inflation of the cuff balloon 1110 reduces the diameter of the vessel 1100 allowing the vessel 1100 to be unloaded, reducing the vessel's operation to a lower region of it's stress strain curve, and thus reducing its stiffness (or pressure-strain elastic modulus $E_p$).

The coupling of the cuff balloon 1110 and vessel 1100 offloads the vessel wall allowing vessel expansion (time dependent systolic pressure dampening), and vessel contraction (boost in time dependent diastolic pressure discharging) via the charging and discharging of the windkessel 1125, thereby restoring the secondary heart pump in the hypertensive, the aged stiffened and diseased stiffened vessel patients, and congestive heart failure patients, and when adjusted the hypotensive patient group such as those experiencing end stage heart failure.

The amount of capacitance or charge and discharge depends on the volume of the Windkessel gas chamber 1104 and the cuff balloon 1110, the pressure threshold used, and the amount of offloading of the wall of the vessel 1100. A reduction in the diameter of the vessel 1100 is required to offload the vessel wall so it follows the movement of the cuff balloon 1110 without restraint thereby creating an efficient energy coupling. This reduction is in the range of 5-15% for an aged healthy vessel. A reduction greater than 15% might be necessary in diseased cases where plaque and aneurysms are present This system allows for adjustment and fine tuning where part of the vessel's stiffness characteristics can be used if so desired.

A variety of sizes of windkessel housings 1125.1 can be used to increase or decrease the volume and size of the compressible gas chamber 1104, if necessary. The patients cardiovascular conditions and vessel stiffness can be measured and entered into a computer program model of the windkessel 1125, vessel, and cardiovascular system, calculating cardiovascular performance and thus determining the correct size of the windkessel compressible gas chamber 1104 and operating conditions prior to implantation.

The average equivalent pressure strain elastic modulus $E_P$ of the applied cuff 1101 in combination with the vessel 1100 segment, is that of healthy young aorta, in the range of $0.2 \times 10^6$ dynes/cm$^2$ to $2 \times 106$ dynes/cm2, but could be $0.1 \times 10^6$ dynes/cm$^2$ to $20 \times 10^6$ dynes/cm$^2$ based on achieving increased clinical benefits.

Multiple sections of a vessel or aorta can be treated in this manner to boost performance for both left and right sides of the heart circulatory systems and vessels. For example a viable approach would be to place separate cuffs 1101 on both the ascending and descending aortas, the separate cuffs 1101 could be deployed to operate with or without a windkessel, the same windkessel, or multiple windkessels or a combination thereof.

Where there is plaque or one or more aneurysms, such cases can be treated with other vessel off loading approaches described, and in combination with any of the embodiments described herein.

Additional Windkessel Features

An addition to the windkessel 1125 could be a system to increase or decrease the bias pressure. Such a system could consist of a syringe piston where the piston is incrementally stepped to increase or decrease the pressure in the windkessel gas chamber 1104 to a set mean operational level. The system could have a micro stepper motor that can be locked into position when set thus only requiring power when the motor is moved. Appropriate control electronics would need to be incorporated which could be battery powered and consist of an electronic sensor to activate changes in response to an externally triggered coded electronic signal.

A second windkessel with a vacuum bias could be used in conjunction with the windkessel 1125 with a positive pressure bias, and be controlled to switch between each, gated by ECG or blood pressure, to act as a pump. Increased cuff operating pressures can then be achievable by increasing each windkessel bias pressure, the positive and negative (vacuum) pressures. Such a system would need volume control (flow per time) measurement in conjunction with the switching control, to maintain the transfer volumes and operating state of each windkessel.

Such a pump system could be configured to control ventricular wall movement to enhance ventricular performance by extra-ventricular compression using external ventricular cuffs. The pump could also be used to inflate an intra-ventricular balloon for blood displacement via a trans-ventricular connection through the ventricle wall.

If so desired, the Windkessel could also be driven by a pump system directly via port 1105 or by replacing the Windkessel housing to drive the diaphragm directly. This could be used if a patient's heart failure progresses at some future time, such a system being applied as an upgrade and making use of previously installed components.

In its simplest form, the windkessel system of FIG. 1 once adjusted, does not require a pump or electrical power to be operated. The electronic add-on systems described above while adding extensions to the system, require only small amounts of power easily delivered over many years of operation from a internal battery source, having an operating life much like an implantable pacer or defibrillator system.

The system is a simple low cost alternative to the high cost more complex extra-aortic counter-pulsation systems and ventricular assist devices on the marker or being developed for market.

Intraluminal Balloon Cuff 1200

Figure 4:
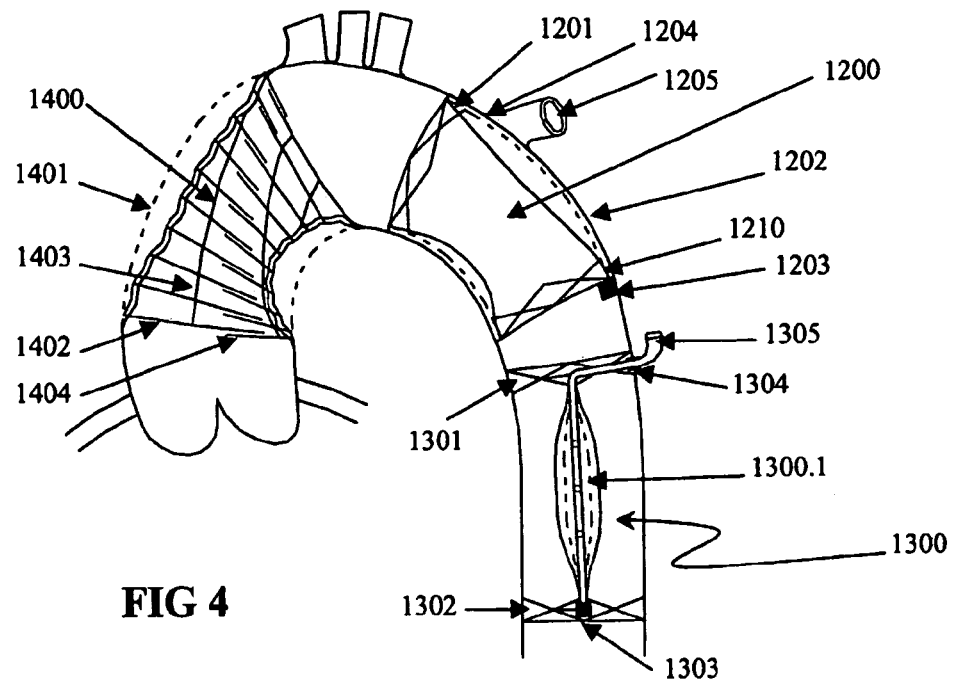
FIG. 4 illustrates an extra luminal stent, an intraluminal balloon cuff, and an intraluminal balloon, at the ascending, upper thoracic, and lower thoracic aorta respectively.

Illustrated in FIG. 4 is an intraluminal balloon cuff 1200 located on an upper thoracic aorta which is held in place by stents 1201 and 1210 at each end, and or glued and or fixed to the inside vessel wall 1202. The cuff 1200 can be pressurised via an internal port 1203 for stand alone operation, or via a transluminal connection 1204 to a extraluminal port 1205 which can be connected to a windkessel housing such as a windkessel 1125 described above.

Intraluminal Balloon 1300

As further illustrated in FIG. 4, there is an intraluminal balloon 1300 located on the lower thoracic aorta, which is held in place by stents 1301 and 1302 at each end having a support member to hold the balloon assembly in the center of the vessel lumen. The balloon 1300.1 can be pressurised via an internal port 1303 for stand alone operation, or via a transluminal connection to an extraluminal port 1305 which can be connected to a windkessel housing such as the windkessel 1125 described above.

The intraluminal balloon cuff 1200 and intraluminal balloon 1300 can operate with or without a windkessel 1125 as described above with respect to cuff 1101 of FIG. 1. The intraluminal balloon cuff 1200 and intraluminal balloon 1300 add a compliant chamber (inflation balloon) into the cardiovascular system without treating the localised vessel stiffness.

The intraluminal balloon cuff 1200 and intraluminal balloon 1300 could be the basis of an intraluminal valve. With an increase in balloon volume and or with elastomeric materials, the balloons could be configured to close off the vessel lumen below a threshold vessel pressure. In the case of 1300, an additional mechanism of moving the balloon ends (or end) closer together would assist occluding the lumen for a valve operation. A spring or sliding mechanism moving the ends closer together may further facilitate this function.

Extraluminal Stent 1400

As is further illustrated in FIG. 4, there is located at the ascending aorta an extraluminal flexible stent 1400, reducing the diameter of the vessel, as indicated by the original diameter represented by broken line 1401, thereby off loading the vessel wall and allowing it to move with, or in agreement with, the movement of the stent 1400. The extraluminal stent 1400 has a series of semi flexible rings 1402 running around the vessel circumference which are inter-joined by cross members 1403. The rings 1402 have a gradual diameter reduction toward the mid-length of the stent 1400, and then an increase in diameter to the downstream end of the stent 1400.

The stent 1400 can be deployed thorascopically by a small incision via its ability to be compressed into a reduced diameter and length. A deployment tool opens up the device diameter and pulls along the length of the extraluminal stent 1400 to facilitate deployment and application around a vessel.

The circumferentially positioned rings 1402 have overlapping struts 1404 at the unjoined sections to better distribute circumferential stress. The overlapping position of the unclosed section, can vary around the circumference of the vessel to further distribute a more even circumferential stress. Both these features attempt to avoid the extraluminal stent 1400 opening around a single portion as would be experienced with a C-shaped application. The average equivalent pressure stain elastic modulus $E_P$ of the extraluminal stent 1400, in combination with the vessel segment when applied, is designed to be that of healthy young aorta, in the range of $0.2 \times 10^6$ dynes/cm² to $2 \times 10^6$ dynes/cm², but could be $0.1 \times 10^6$ dynes/cm² to $20 \times 10^6$ dynes/cm² based on achieving increased clinical benefits.

The extraluminal stent 1400 can be made of shape memory alloys such as Nitinol or shape memory polymers, or could be expanded with a strut pulling tool.

The above described device could be used at any vessel site for the load reduction of a vessel or sac wall, including stiffened vessels and for compressing aneurysm diameter sizes, used alone or in conjunction with other devices described herein or with other endovascular treatments.

For treatment of stiffened vessels to gain systolic load reduction and improve diastolic pressure discharge, vessel reductions in diameter and or cross sectional area of between 1% and 15%, and preferably in the range of 5% to 10%, are expected. The extraluminal stent 1400 can grip the vessel wall directly but could also be sutured onto the vessel adventitia using the existing struts or by including connectors on the ends of the stent to allow for this. Suturing the extraluminal stent 1400 to the wall at the opened section would further distribute circumferential stress more uniformly. For treatment of aneurysms where vessel rupture avoidance is the primary focus, vessel reductions much larger are likely. A large reduction in diameter could be achieved by allowing the stent end sections to have significant overlap when the reduced final diameter is reached. This allows large diameter aneurysms to be reduced to a normal diameter. In such cases, a slow release constricting extraluminal stent could allow the wall to adapt over time to the reduction taking place.

Intraluminal Stent 1500

Figure 5:
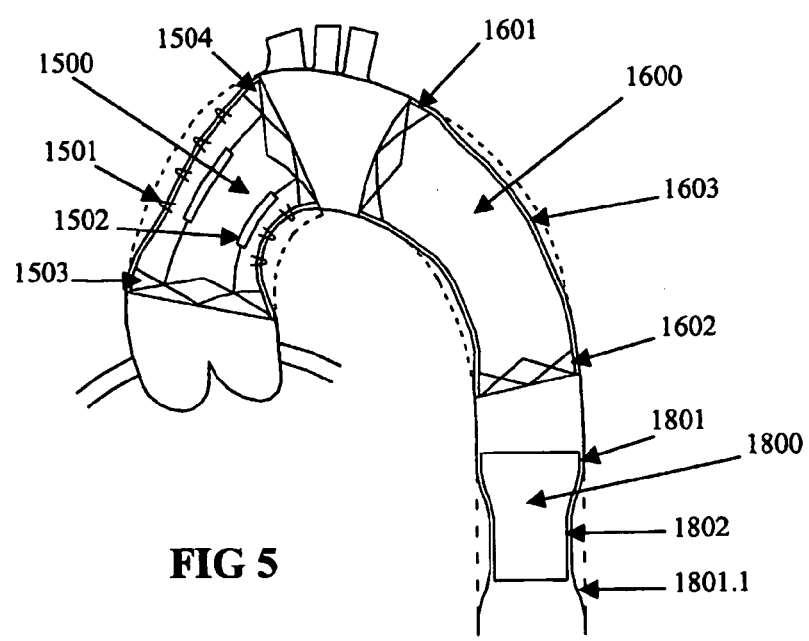
FIG. 5 illustrates an intraluminal stent, an intraluminal graft stented at both ends, and intraluminal graft, at the ascending, upper thoracic, and lower thoracic aorta respectively.

Illustrated in FIG. 5 is a vessel constricting intraluminal stent 1500 which is shown as being deployed in an ascending aorta The stent 1500 uses either hooks 1501 attached to flexible stent strut members and or stent strut feet 1502 glued against the inside vessel wall acting to pull the vessel wall inwards thus reducing the diameter and thus the load on the vessel wall at physiological pressures.

The stent 1500 has rigid or semi rigid ends 1503, 1504, which fix the entire stent 500 against the vessel wall at the vessel's current diameter, with a series of flexible members in the mid-section which have a reduced diameter thereby pulling the vessel inward and reducing its diameter at physiological pressure.

The average equivalent pressure strain elastic modulus $E_P$ of the intraluminal stent 1500 when deployed in a vessel segment is such that the combination of the stent's properties and the vessel wall properties equates that of healthy young aorta, which is in the range of $0.2 \times 10^6$ dynes/cm² to $2 \times 10^6$ dynes/cm² but could be $0.1 \times 10^6$ dynes/cm² to $20 \times 10^6$ dynes/cm² based on achieved increased clinical benefits.

The intraluminal stent 1500 can be made of shape memory alloys such as Nickel Titanium, Nitinol or shape memory polymers, or stainless steels and thereby expanded with an inflation balloon catheter system deployed via standard endovascular femoral artery access.

The stent 1500 could be used at any vessel site for the load reduction of a vessel or sac wall, including stiffened vessels and for potentially treating aneurysms, used alone or in conjunction with other endovascular treatments. The reduction in diameter for the offloading of a stiffened otherwise healthy vessel is between 1% and 15%, and preferably in the range of 5% to 100%, or possible greater when the vessel has plaque, at normal physiological pressure. The reduction in diameter for the treatment of aneurysms is likely to be significantly larger.

Endograft 1600

Also illustrated in FIG. 5 is an endograft 1600 with rigid or semi rigid end stents 1601, 1602, and a flexible elastic mid-section 1603 which is located in the upper thoracic aorta of FIG. 5. The endograft 1600 has a reduced diameter 1603 in the mid-section to facilitate the reduction in the surrounding outer vessel diameter necessary to reduce the stiffness of the vessel, reducing the vessel's stress-strain profile.

The average equivalent pressure strain elastic modulus $E_P$ of the mid-section 1603 within the vessel is designed to be that of healthy young aorta, in the range of $0.2 \times 10^6$ dynes/cm$^2$ to $2 \times 10^6$ dynes/cm$^2$ but could be $0.1 \times 10^6$ dynes/cm$^2$ to $20 \times 10^6$ dynes/cm$^2$, based on achieving increased clinical benefits. The reduction in diameter for the offloading of a stiffened otherwise healthy vessel is between 1% and 15%, and preferably in the range of 5% to 10%, or possibly greater when the vessel has plaque, at normal physiological pressure.

The deployment of the endograft 1600 may include gluing it into the vessel to pull the vessel down to the smaller diameter if necessary, and would then typically be held in place at its ends by intraluminal stents 1603, 1604 as shown. However, sealing and fixing at the end section may also be by gluing the outer graft to the inside vessel wall.

The end stents 1601 and 1602 of FIG. 5 can be used to increase the graft diameter to the vessel diameter, and increase the vessel diameter to a desired operation range, leaving the smaller diameter mid-section to operate as described.

Endograft 1800

Illustrated in FIG. 5 is an endograft 1800 located in a lower thoracic aorta consisting of two sections. A first section 1801 seals and fixes the endograft 1800 to the inside wall of the vessel, (which can be done with or without the use of an intraluminal stent), while a second section 1802 has a reduced diameter. The distal end is not sealed or fixed against the vessel 1801.1. This approach can offer some benefit to reducing the pressure strain elastic modulus $E_p$ of a vessel and enhancing elasticity and recoil during diastole. This approach may be beneficial where length and vessel geometry does not allow for a full length graft and or when the distal end overlies plaque or one or more aneurysms and fixing with a stent or glue is not desirable.

Device 1800 could be designed to function like a valve. The second section 1802 would reduce its diameter below a threshold pressure, allowing the section to close onto itself, and expanding its diameter in response to pressure rising above the threshold, thereby opening the section. An elastomeric material of high compliance would be required.

Endograft 1700

Figure 6:
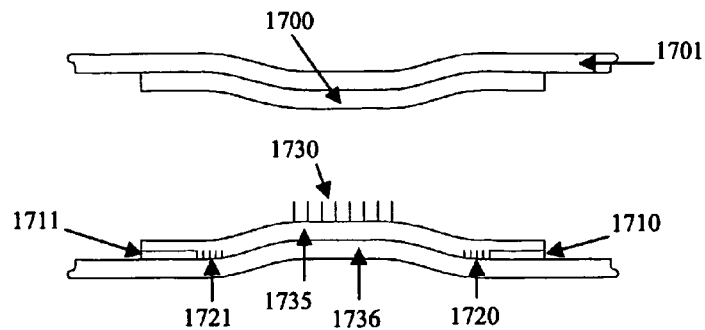
FIG. 6 illustrates a cross section through a vessel having an intraluminal graft located therein.
Figure 7:
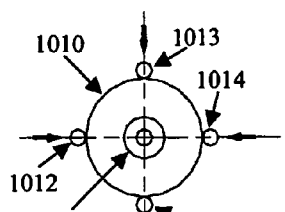
FIGS. 7, 7A, 7B, 7C and 7D are a series of illustrations showing a method of compressing an intraluminal graft, such as that illustrated in FIG. 6, onto a balloon deployment catheter.
Figure 7A:
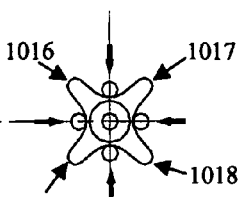
Figure 7C:
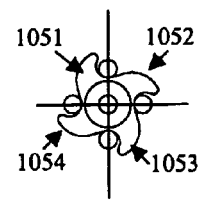
Figure 7B:
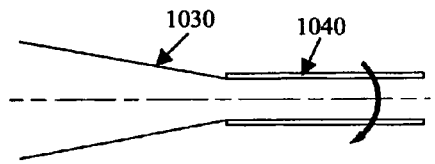
Figure 7D:
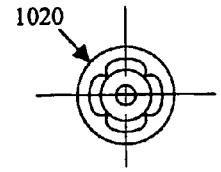

Illustrated in FIG. 6, is a cross section through the wall of a vessel 1701 which has an endograft 1700 positioned therein. The endograft 1700 has additional separate end sealing sections 1710, 1711 for sealing, and fixing sections 1720, 1721 having fixing or anti-migration means. The end sections of the endograft stent 1700 have an outer, highly compliant, polymer layer that compresses against the internal surface of the wall of the vessel 1701 when outwardly urged by intraluminal end stents 1601, 1602 (as illustrated in FIG. 5) used at each end.

The fixing sections 1720, 1721 consist of indentations or holes or pores in the outer graft material to produce an effect similar to a textured surface. Such an effect is believed to promote cellular growth inwardly of the wall tissues into the outer surface of the graft 1700 and therefore assist in holding or fixing the graft 1700 in place with time and reducing long term graft migration.

The inside of the endograft 1700 can consist of a textured surface 1730 along part or all of the inner surface which will promote neo-intima formation and potentially endothelial and smooth muscle cell generation much like a native vessel wall.

The endograft 1700 has a mid-section with a reduced diameter 1735 to allow offloading and therefore contraction of the surrounding vessel 1736, allowing the stiffness reduction as described above. The sealing and fixing sections can add short and long term additional benefits, but as described the endograft 1700 can be glued inside the vessel wall to achieve desired sealing and fixing and therefore the endograft 1700 may not have these end sections. The mid-sectional reduction uses sealing and fixing in order to operate.

Figure 34:
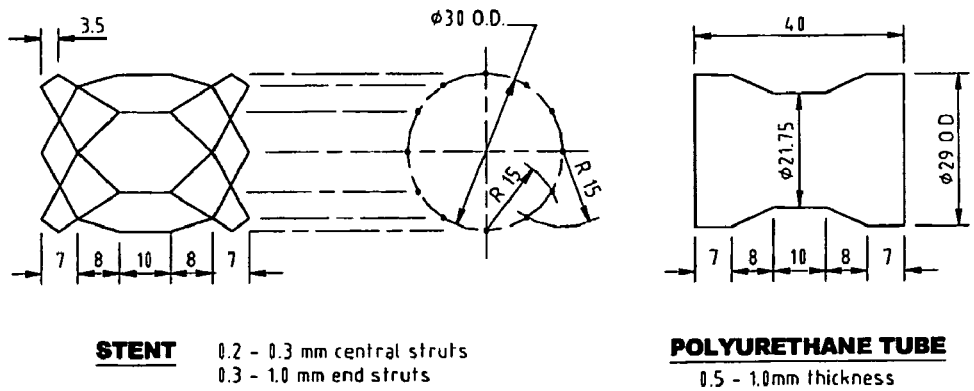
FIG. 34 is a technical drawing of a stent and graft design.
Figure 34:
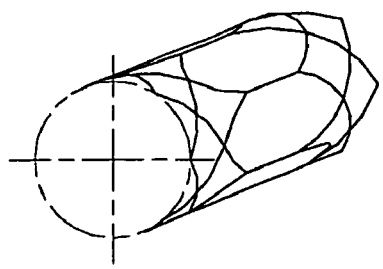

While both endografts 1600 and 1700 could be deployed and adhered to the vessel wall by glue whilst pushed against the vessel wall with a deployment balloon, both as said can have stents fixing each end section against the wall with intraluminal stents such as end stents 1601 and 1602. These stents can be balloon and self expandable as a secondary procedure after graft deployment. A stent that ranges over the entire graft could also be used to support the end sections, having a series of compliant members in its mid-section to allow the graft mid-section diameter reduction to be maintained and allow expansion and contraction during systole and diastole in response to pressure changes. This would allow the supporting stent to be deployed as one piece minimising or reducing potential alignment problems. Such a design is shown in FIG. 34.

Coating of various types can be used on all surfaces to control desired blood compatibility and enhance the growth of endothelial cells.

The above described endografts are preferably made from polyurethane, silicone, or a polyurethane and silicone combination material or other shape memory thermoplastics or polymeric materials, and or fibre reinforced polymers.

If desired, injection of heat activated gels or thermosetting materials could be injected into a balloon-like mould in situ. This removes the problem of a thick large diameter graft being a challenge for femoral artery deployment due to its more difficult compression and diameter reduction. This problem could also be reduced by use of accessing the femoral artery higher up towards the iliac arteries where its diameter is larger, or even a more advanced vascular access point using larger vessels.

The graft could also be inflated with a medium consisting of a biocompatible fluid such as liquid silicone or saline, containing a contrast agent (x-ray viewable). For inflation prior to implanting, the inflation media can consist of a gel solution that expands with temperature to a final operating volume at 37° degrees Celsius. Uncured or liquid polymer can be used to inflate the balloons, which is thermoset, preferably at a quick pace, at 37° C. (or via activation eg. light/heat) resulting in said section having effective compliance or cushioning properties.

The inflatability of the balloon can be used so as to adjust or set the modulus of elasticity of the treated section. The inflation could be performed by the introduction or use of: liquid or gel which will expand to its operational volume and modulus of elasticity. This could be done before deployment, but preferably after deployment using heat activated gels, or the pumping in of saline; water; silicone; an agent which will receive a contrast medium; elastin; collagen; elastin and collagen in combination; or air, or a polymer that cures or thermosets after injecting.

The highly compliant material could be stretched to very large diameters to grab, attach, adhere and or seal larger diameter aneurysm sacs and pulling them into a reasonable and safe diameter whilst unloading and removing the risk of rupture.

The treatment site or sites may require repair due to one or more of the following: aortic stiffening; atherosclerosis; plaques; blockages; aneurysms; reduced load bearing capacity; rupture; pressure regulation, heart valve problem; or intestinal disorders.

The method can include the step of said device being compressed or contracted for the purpose of positioning said device at said site, such as that described below.

Endograft Deployment System

Illustrated in FIGS. 35, 7, 7A, 7B, 7C, and 7D is a deployment method and device to reduce a larger diameter, elastomeric endograft 1010 into a working deployment diameter 1020. The graft is placed inside the loading mechanism 1060 over a balloon arterial access catheter 1011. Four pins 1012, 1013, 1014, 1015 at equal points around the circumference of the graft 1010 constrict the graft 1010 towards the catheter 1011 positioned in the lumen of the graft up to the catheter. The pins are moved by a motor system 1061, such as a stepper motor, attached to a sliding mechanism 1062, such that when the motor rotates, a threaded shaft moves the connected pin inward. The resulting four lobes 1016, 1017, 1018, 1019 of the graft are then wrapped around the four pins by a rotating cone sliding over the graft thereby winding the graft lobes over the pins 1051, 1052, 1053, 1054 and reducing the diameter. The assembly is moved away from the pins so that the pins are removed as the cone approaches the final diameter of the compressed graft, assembly sliding the compressed graft into a sheath 40, which will remain on the catheter until deployment. A non toxic lubricating agent such as silicone oil can be applied to the inside surfaces of the cone and sheath to reduce friction and allow the graft reduction without catching on the graft material.

This arrangement can also be applied to the reduction for deployment of stents with or without a graft. In such cases the cone could be rotational or non-rotational, for stents, grafts, or stent-graft compression onto a balloon catheter delivery system prior to deployment. For stent compression, the 4 pin reduction step may not be required as the stent could be compressed with direct application of the cone.

Once at the located site, the sheath in removed, and the balloon is inflated to unwrap the graft into its final diameter and push it against the vessel wall, holding it in position until it is stable and allowing the adhesion of the wall to the outer graft surface in the case of using glue, possible a heat activated, or blood or fluid activated glue. The catheter delivery system could have a lumen and ports upstream and downstream of the graft section, allowing the passing of blood to enter into the upstream port, pass through the catheter lumen, and out the downstream port back into the blood stream. This would allow for extended balloon inflation times without completely stopping blood flow downstream of the treated section. Once the graft is in place, the stents positioned at the graft ends offering further sealing and fixing, can be deployed as necessary.

Intraluminal Stent Graft 10

Figure 11:
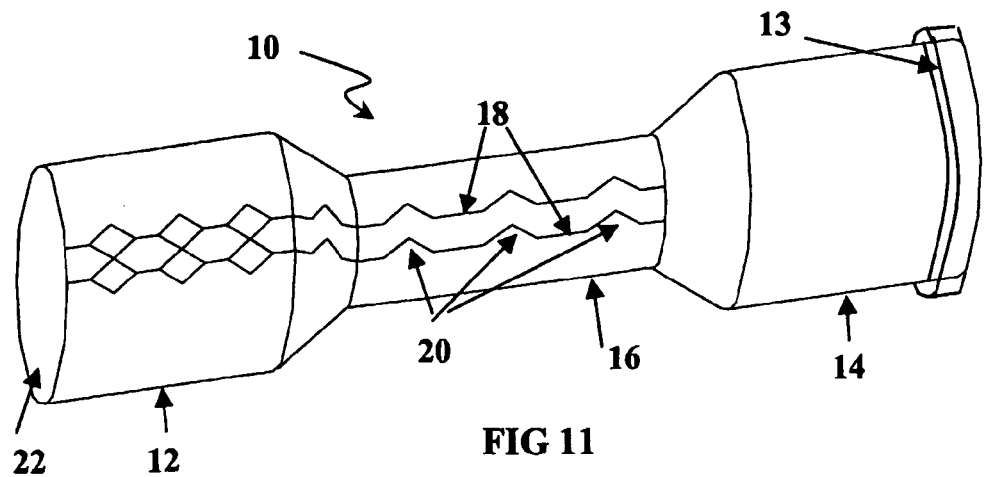
FIG. 11 is a schematic representation of an intraluminal device.

Illustrated in FIG. 11 is an intraluminal stent graft 10 which has three sections, the first and third sections being two stent ends 12 and 14. The stent ends 12 and 14 are rigid or semi-rigid, in that for deployment of the stent graft 10, the stent ends 12 and 14 are collapsible for deployment purposes but provide rigidity when deployed.

The intraluminal stent graft 10 is designed to increase arterial compliance for cases where aortic stiffening has disrupted cardiovascular dynamics. The stent graft 10 will be used in the arterial system to reduce heart load and assist in restoring coronary arty perfusion and to add compliance to a section sealing off an aneurysm.

The intraluminal stent graft 10, consists of stent ends 12 and 14 forming outer stented sections to provide the required mechanical rigidity. The stent graft 10 is preferably lined with a blood contacting elastomer. Each stent end 12 and 14 provides a non-compliant section which will push against the internal tubular section of the vessel wall providing a seal between the wall and the outside of the stent graft 10.

The second of the three sections is the intermediate section 16 of the stent graft 10, which is illustrated as having a reduced diameter. The intermediate section 16 consists of a compliant section with a pressure strain elastic modulus $E_P$ similar to healthy aorta (healthy aorta $E_P$ is $0.40 \times 10^6$ dynes/cm$^2$ at a physiological pressure of 120/70 mmHg), but can be more or less rigid or elastic as required.

The compliant intermediate section 16 has elongated stent struts 18 which are not cross linked as in the stent ends 12 and 14. The lack of cross linking, and the provision of gathered portions or spikes 20, allow the struts 18 to expand in length that allows radial, axial and circumferential expansion of the struts and compliant elastomer from the mean diameter. The pressure strain elastic modulus $E_P$ of the intermediate section 16 will thus be determined by a combination of both the struts 18 and the elastomeric material which exists on the inside of the struts 18. This involves the mean diameter reduced to approx. 80% (could be 5%-50%) of the end sections at diastolic pressure, allowing the expansion of this compliant intermediate section 16 during systole without loading the vessel wall, and thereby having a stiffness independent of the "stiffened" aortic wall. Using different combinations of components, a section where the luminal diameter is increased by up to 30% or greater may be possible and provide clinical benefit.

The stent ends 12, 14 and the intermediate section 16, form an exoskeleton around the outside of the elastomeric tube. If desired or required, a foam annulus 13 can be used to provide a seal between the inside surfaces of the tubular wall of the vessel. The stent ends 12 and 14 of stent graft 10 would seal against the foam, likely to be attached prior to deployment.

The second or compliant intermediate section 16 can be partially around the circumference.

The stent graft 10 will be compressed into a small diameter allowing intraluminal or endo-luminal delivery such as endovascular delivery via the femoral artery. An encasing sheath (not illustrated) holds the device in the compressed state.

Using endovascular guide wires and x-ray monitoring, the stent graft 10 will be moved into position using the guide wire while in its compressed state. When positioned the device will be released from the deployment mechanism by sliding the sheath off and pushed into its operational diameter via inflation of an underlying balloon pressurised by an externally fitted manual balloon pump. The device could alternatively be deployed by either: self-expandable means; shape memory expandable means; balloon expandable means; or a combination of these.

Compliant elastomers could be reduced by use of a vacuum, contracting the elastomer onto an underlying mandrel, or a chemical agent that contracts the material.

Inflatable Stent Graft 110

Figure 12:
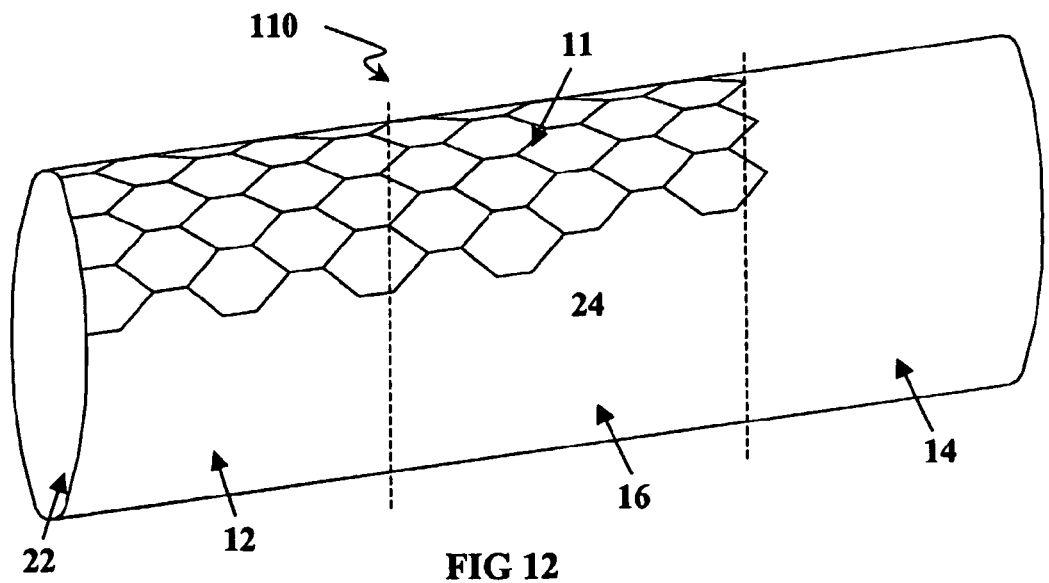
FIG. 12 illustrates a diagrammatic representation of an intraluminal device similar to FIG. 11 but constructed differently.
Figure 13:
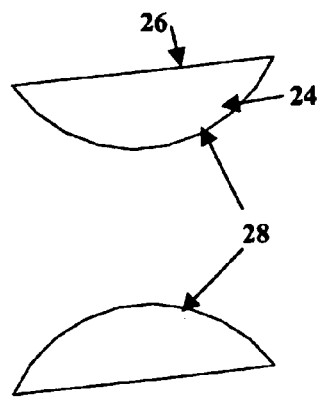
FIG. 13 illustrates a cross section through the inflatable section of FIG. 12.
Figure 14:
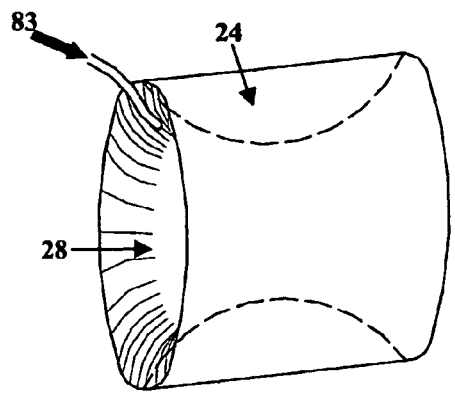
FIG. 14 illustrates a diagrammatic perspective view of the inflatable section of the intraluminal device of FIG. 12.

Illustrated in FIGS. 12 to 14 is an inflatable stent graft 110, consisting of an outer stented exoskeleton providing mechanical rigidity. The exoskeleton 11 is lined with a blood contacting elastomer. Between the elastomer 22 and the skeleton 11 is a compliant inflatable pillow 24 which is of a length to cover the intermediate section 16. These component parts seal together and could be deployed as separate pieces or preassembled as a single unit. The compliant inflatable pillow 24 can have a port 83, whereby the pressure strain elastic modulus $E_P$ can be set or adjusted after deployment.

The ends 12 and 14 form a non-compliant base which will push against the vessel wall providing a seal between the wall and the outside of the device. The compliant inflatable pillow 24 of the intermediate section 16 of the inflatable stent graft 110 is an air, liquid, or gel filled cylindrical double wall section that allows compression at physiological blood pressure levels.

The outer layer or outside circumference 26 of the compliant inflatable pillow 24 seals against the inside of the stent-graft skeleton 11 and is rigid enough so it doesn't distort under loading. The inside walls 28 can have a blood contacting surface which is flexible and elastic so that when loaded it can deform proportionally to the applied pressure, absorbing an energy charge during systole, then releasing the energy charge during diastole. The stiffness or pressure strain elastic modulus $E_P$ of the combined inner surface with the compliant inflatable pillow inflated, is likely to be within the range of healthy to stiffened vessels, i.e. $0.4 \times 10^6$ dynes/cm$^2$ to $20.0 \times 10^6$ dynes/cm$^2$ at a physiological pressure of 120/70 mmHg. However, the material stiffness of the outer layer 26 and inside walls 28 used to form the compliant inflatable pillow 24, can vary outside of this range.

The compliant inflatable pillow 24 can reduce the diameter of the second or intermediate section 16 by 5% to 50% of the diastolic diameter. In the case of a gel or other filling the compliant inflatable pillow 24, the gel can be selected so as to be heat activated, whereby it will expand to its operational volume and pressure strain elastic modulus ($E_P$) after deployment and contact to 37° C. temperatures.

Such a gel, or liquid which could be used for this includes: saline, water, silicone, elastin, collagen, a combination of elastin and collagen, other agents with contrast medium.

An advantage of the inflatable stent graft 110 is that absorbing energy during systole and recoil during diastole is possible without loading the vessel wall, and thereby having an equivalent stiffness independent to the "stiffened" aortic wall.

If desired, the compliant pillow section 24 can by located partially around the circumference of the inflatable stent graft 110.

The inflatable stent graft 110 can be deployed in a manner similar to that described above in respect of the stent graft 10. If desired, the compliant inflatable pillow 24 alone can be positioned within a vessel provided there is adequate sealing and fixing between the outer circumference 26 of compliant inflatable pillow 24 and inside of the vessel. In the case of the compliant inflatable pillow 24 being positioned by being sutured in place in a tubular or sac wall, by a single end, the device will consist of two sections, the securing section and the inflatable compliant section. If the compliant inflatable pillow 24 is secured by both its ends then the device will be considered to have three sections: the first and third being for securing the device and the intermediate or second section being the compliant or inflatable section.

Endograft 210

Figure 15:
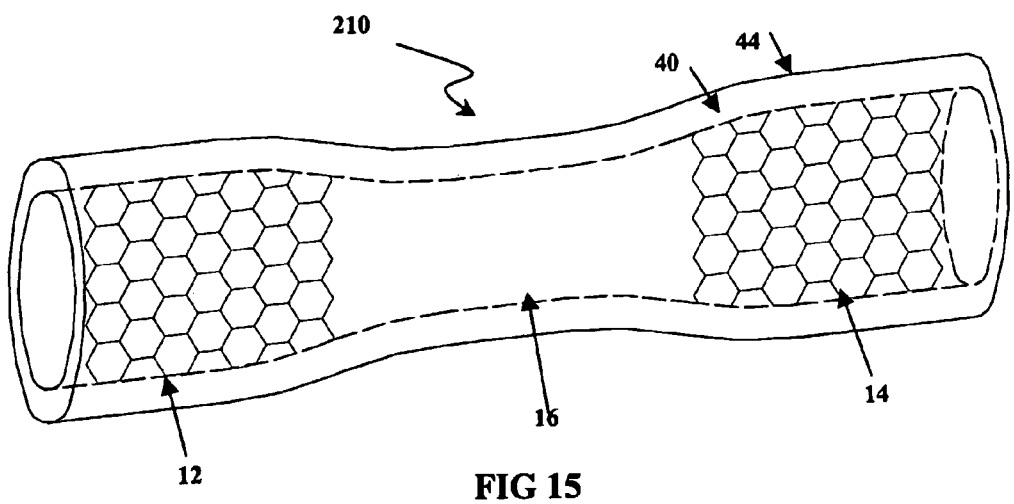
FIG. 15 is a diagrammatic representation of another intraluminal device.

Illustrated in FIG. 15 is an endograft 210 which consists of an outer elastomer 40 with inner stented ends 12 and 14. The ends 12 and 14 are firmly pushed against the inner surface of the elastomer 40 which seals the outside surface 44 of the elastomer 40 to the vessel wall. The inner section of the elastomer holds its nominal diameter at physiological pressure, that of 5% to 50% of the vessel diameter at Pdia, and can expand during systole and recoil during diastole. Material stiffness or pressure strain elastic modulus $E_P$ ranges from healthy aorta to that of a stiffened vessel ($0.4 \times 10^6$ dynes/cm$^2$ to $20.0 \times 10^6$ dynes/cm$^2$ at a physiological pressure of 120/70 mmHg).

The compliant intermediate section 16 can be of reduced diameter or if desired without any reduction in diameter. Further the compliant section intermediate 16 can have a flexible stent-strut lining joining the rigid stent end sections 12 and 14. The compliant intermediate section 16 can also have flexible stent-strut on the outside lining, as well as the rigid stent end sections 12 and 14.

Figure 16:
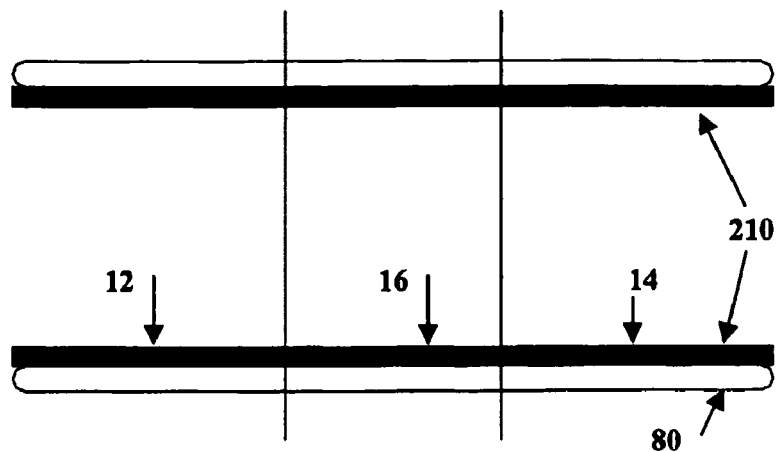
FIG. 16 is a diagrammatic representation of the intraluminal device of FIG. 15 implanted in an endoluminal manner.

Illustrated in FIG. 16 is a cross section through the endograft 210 of FIG. 15. The endograft 210 has no reduced diameter in the second or compliant intermediate section 16, while the stent sections 12 and 14 provide the means to adhere and seal the endograft 210 into the tubular wall 80.

A stent-graft can be used as a foundation prior to the endograft 210 being deployed.

Deployment of the endograft 210 will be as previously described in relation to the intraluminal stent graft 10 or inflatable stent graft 110. The stent in the endograft 210 will be encased in or attached to the elastomer, and compressed ready for deployment as a single piece.

Various combinations of the above features of the intraluminal stent graft 10, the inflatable stent graft 110 and endograft 210 can be used: for example the compliant inflatable pillow 24 could be on the outside of the devices 10, 110 and 210, or on the outside of the vessels.

To manufacture the intraluminal stent graft 10, the inflatable stent graft 110 and endograft 210, the materials selected should be bio-stable. Thus, for the stent constructions, i.e. ends 12, 14 and struts 18, the following materials might be used: Stainless Steel, Nitinol, and suitable Polymers. The struts 18 could be of the order of 0.25 mm to 1 mm thickness (however greater or lesser thickness might be used depending upon the desired result).

In respect of the elastomeric materials which can be used with the devices 10, 110 and 210, these could be selected from: polyurethane (eg. CHRONOFLEX®, BIOSPAN® and CORETHANE®), or silicone (eg. Dow Corning range). The variation in thickness used can be between 0.25 mm to 1.5 mm (or a possibly greater range), while the pressure strain elastic modulus $E_P$ can vary between $0.40 \times 10^6$ dynes/cm$^2$ to $20.0 \times 10^6$ dynes/cm$^2$ at a physiological pressure of 120/70 mmHg.

Blood contacting surfaces can be treated or have finishes that reduce thrombus formation, and stimulate endothelial cell growth.

Use of anticoagulants are envisaged until thrombus formation risk is minimised.

For treatment of a decrease in arterial compliance, the intraluminal stent graft 10, the inflatable stent graft 110 and endograft 210 can be deployed into the ascending aortic section via femoral access using an endovascular delivery system. The intraluminal stent graft 10, the inflatable stent graft 110 and endograft 210 could also be deployed in other sections of the aorta.

Surgically Deployed Prosthesis 310

Figure 17:
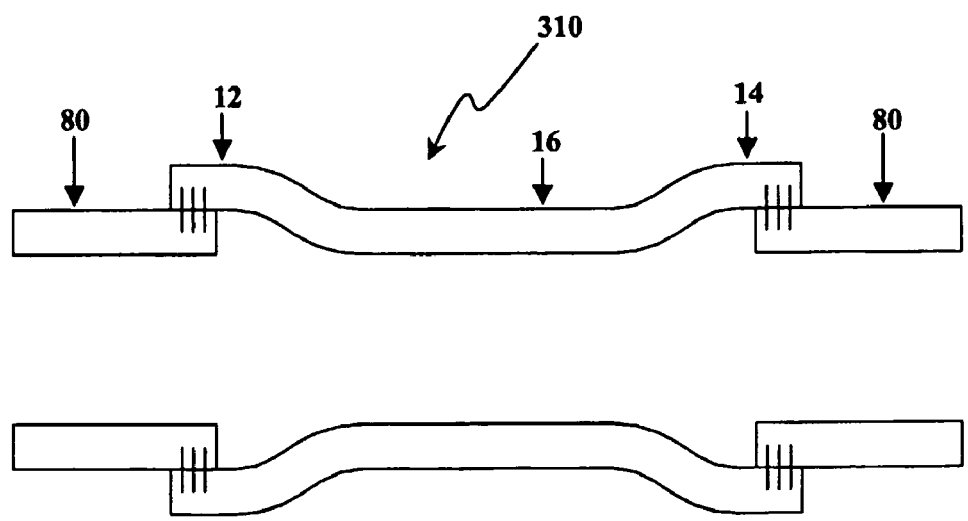
FIG. 17 is a diagrammatic representation of the cross section of an intraluminal device deployed by surgical means.
Figure 18:
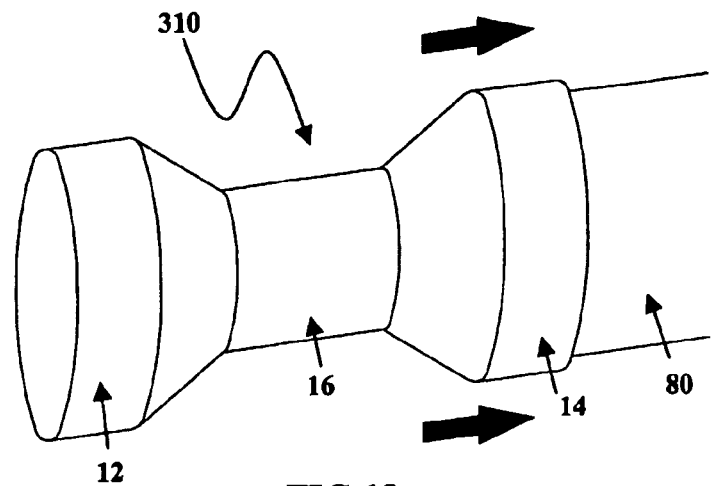
FIG. 18 is a diagrammatic perspective of the device of FIG. 17 deployed by surgical means.

As illustrated in FIGS. 17 and 18, a device 310, similar to a stent graft 10, 110 or 210, can be applied as a surgical prosthesis. That is a compliant intermediate section 16 is provided, but end sections 12 and 14 allow fitting to a blood vessel 80 or an aorta via sutures and or physiological glue. The device 310 shown in FIGS. 17 and 18 is a graft device, not an intraluminal device. The second or inflatable section could be internally or externally fitted to the device or to the stent grafts of previously described devices. In the case of a stent-graft, inflation system could be fitted inside or outside the stent-graft but intraluminal to vessel, or fitted extraluminally to vessel, whether around the vessel pushing on the vessel with or without internal stent-graft.

If desired the second or intermediate section 16 can be a fibre reinforced elastomer. The fibre can be used to reinforce the compliant intermediate section 16. Such fibre can be polytetrafluoroethylene (PTFE), GORTEX®, or DACRON®. These materials can also be used on the stent sections 16, 12 and 14.

Active Inflation Control System 410

Figure 19:
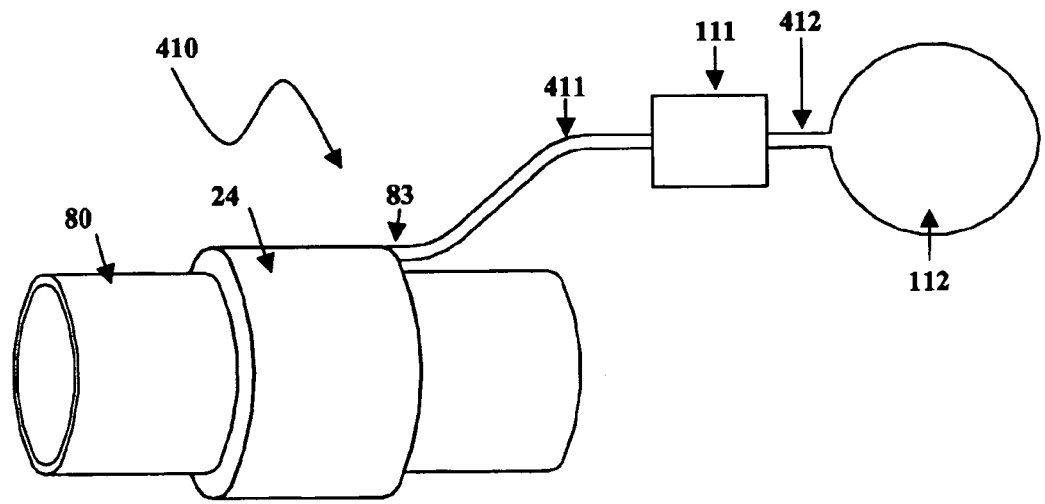
FIG. 19 is a schematic representation of an extraluminal or intraluminal inflation system which can be used with a device.

The compliant inflatable pillow 24 of FIGS. 13 and 14 can be such that pressure in the system is preset via the port 83 so as to provide a passive control system. However, in FIG. 19, there is illustrated a system 410 which includes a compliant inflatable pillow 24 sutured into place as a union between the cut ends of a blood vessel 80, with the section of decreased compliance having been removed. Alternatively, the compliant inflatable pillow 24 could be deployed intraluminally or extraluminally depending upon need This is similar to the grafts 110, 210 or 310 of previous Figures.

The system 410 also includes a valve 111 and a diaphragm 112 and a conduit 411 and 412, linking the port 83, the valve 111 and the diaphragm 112 so as to provide active control whereby the pressure strain elastic modulus $E_p$ of the compliant inflatable pillow 24 can be adjusted to optimum, or as required.

Such a system may operate after adjustment of the valve, possibly a 2-way valve Electronic valve control could also be used by including an internal pressure sensor within the pillow or the inflation line leading to the pillow. The measured compliant inflatable pillow 24 pressure would then activate the appropriate valve control using electronic means. More advanced control may be achieved with advanced electronics or a CPU to automate the adjustment process in response to sensed environmental characteristics, such as body temperature, heart rate, blood pressure and other bodily characteristics.

Valve control could allow for different elastic properties between the "charge" (systolic phase) and "discharge" (diastolic phase) phases of the cardiac cycle. This will allow a visco-elastic response that closer resembles the native healthy aorta to be achieved. While the above description is directed to the use of the devices 10, 110, 210 and 310 in respect of arteries, it will be readily understood that the embodiments of the invention could be used with veins, and any other tubular walls such as the urethra, or intestines.

The devices and methods described above can be used to address the following difficulties: hypertension and aortic stiffening by means of the above described compliant prothesis in stent-graft or graft form, and the tubular wall compliance device.

Two Section Device 510

Figure 20:
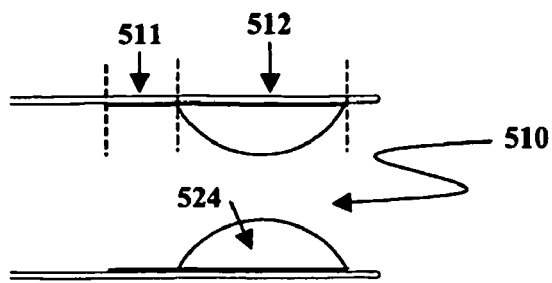
FIG. 20 illustrates a schematic cross section of an implanted two section device.

Illustrated in FIG. 20 is a device 510, which is comprised of two sections, a first section 511 and a second section 512. The first section 511 is used to secure the device 510 to the tubular wall. The second section 512 is an inflatable pillow 524 (but could be simply tubular in nature), and provides the compliance to the tubular wall.

Five Section Device 610

Figure 21:
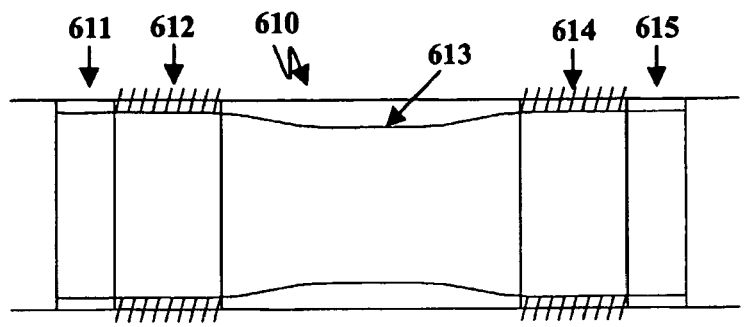
FIG. 21 illustrates a schematic cross section of an implanted device having five sections.

In the device 610 illustrated in FIG. 21, there are five sections, whereas the devices of FIGS. 11 to 18 have three sections. The device 610 is similar to the stent graft 10 in that there is an intermediate compliant section 613, which has on either side, first and third sections being securing (or adhesion) sections 612 and 614, which are illustrated in FIG. 21 as being glued or sutured into position to the tubular wall in which the device is inserted. On the outboard side of the sections 612 and 614 are fourth and fifth sections being sealing rings 611 and 615. The rings 611 and 615 can be of a foam or other bio-compatible material to assist with the sealing of the sections 612 and 614, and thus the device 610, to the tubular wall. In the device 610, the sections 611 and 615 are adjacent to the respective sections 612 and 614.

Three Section Device 710

Figure 22:
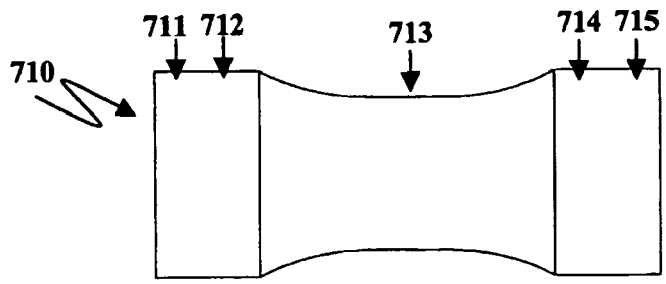
FIG. 22 illustrates a schematic of a device having five sections with the two end sections being combined.

Whereas, in FIG. 22, the device 710 has sections 711 and 712 that are superimposed or combined, as are the sections 714 and 715. This produces a three section device 710.

Standard Graft 800 Combined with a Compliant Graft

Figure 23:
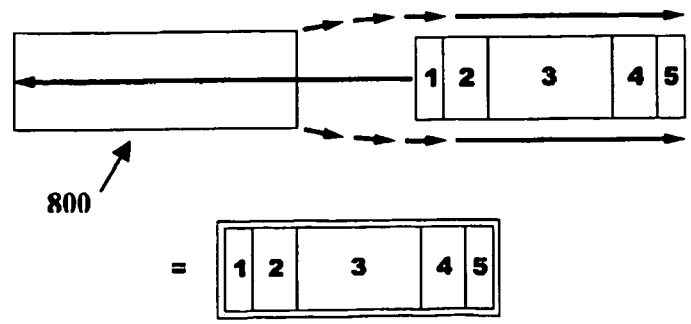
FIG. 23 illustrates a compliant stent graft combined with a standard graft with the complaint graft being within the standard graft.
Figure 31:
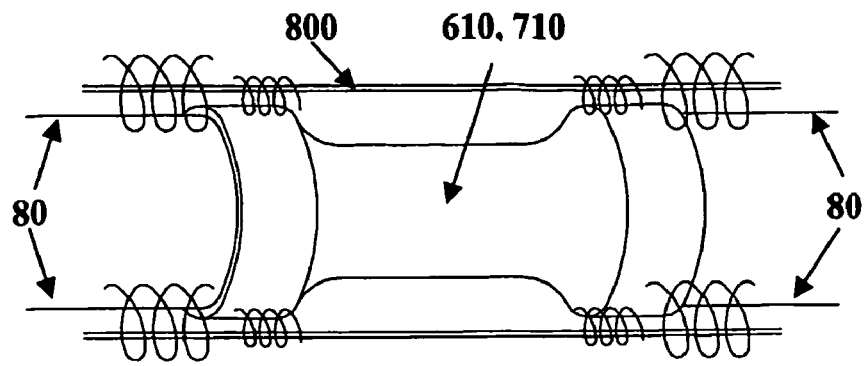
FIG. 31 illustrates a schematic cross section through combined standard graft and a compliant stent graft, deployed between the ends of a severed blood vessel.

Illustrated in FIG. 23 is a combination of a compliant stent graft device such as devices 610, 710 as illustrated in FIGS. 21 and 22, where a standard graft 800 is combined with the compliant stent graft 610 or 710 to produce a compliant graft. The compliant stent graft 610 or 710 can be adhered to the length of the standard graft 800 as illustrated in FIG. 31. The combined standard graft and compliant stent graft can then be deployed as in FIG. 31 by suturing or otherwise adhering the ends of the standard graft as illustrated in FIG. 31 (or the ends of the compliant stent graft) to the ends of a blood vessel 80.

Figure 29:
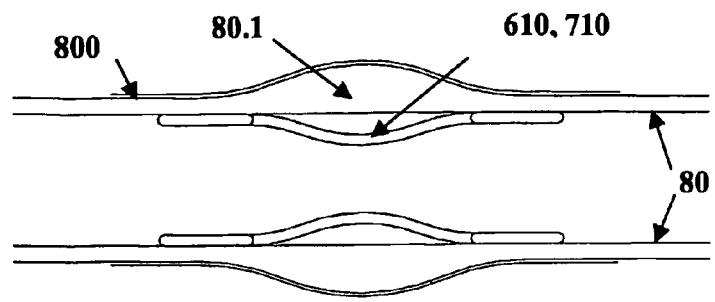
FIG. 29 illustrates a schematic cross section through a combined standard graft and compliant stent graft sandwiching a blood vessel affected by plaque or an aneurysm.
Figure 30:
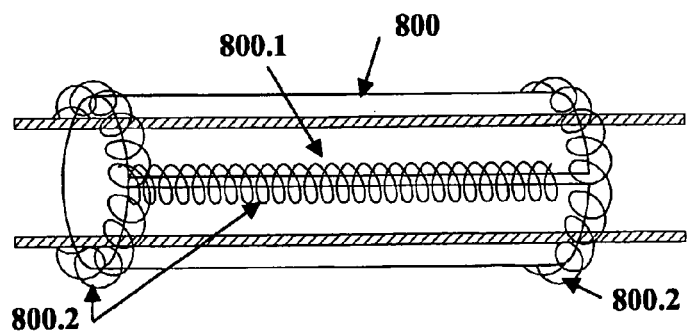
FIG. 30 illustrates an external perspective view of the combined standard graft and compliant stent graft of FIG. 29.
Figure 35:
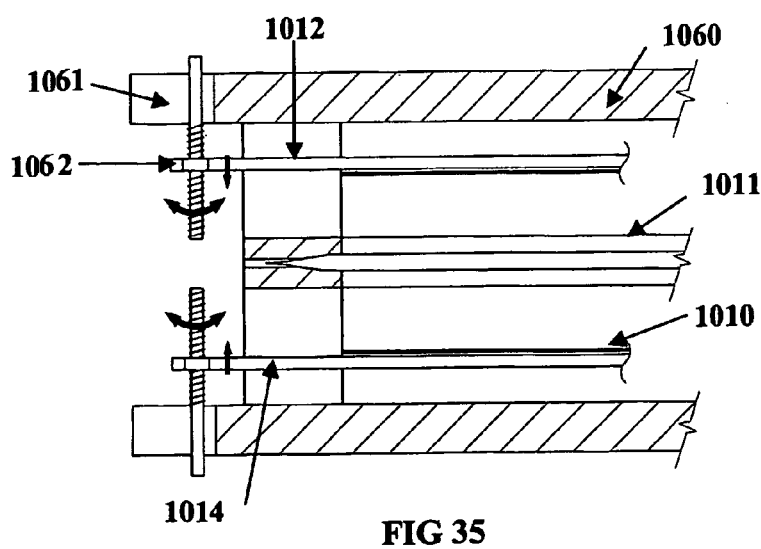
FIG. 35 illustrates a part of the graft compression system detailed in FIG. 7.

Further, a compliant stent graft 610 or 710 can be deployed within the tubular wall 80 of a vessel as illustrated in FIG. 29 which has been affected by plaque or an aneurysm represented by item 80. 1. Then a standard graft 800 is cut at 800.1 and positioned over the affected site and sutured by sutures 800.2 around the tubular vessel 80, as shown in FIG. 30, to provide a combined compliant stent graft 610 of 710 and standard graft 800 which sandwiches the tubular wall 80 of the vessel. This treatment could also be used where plaque or an aneurysm is not present.

AAA Stent Graft

Figure 24:
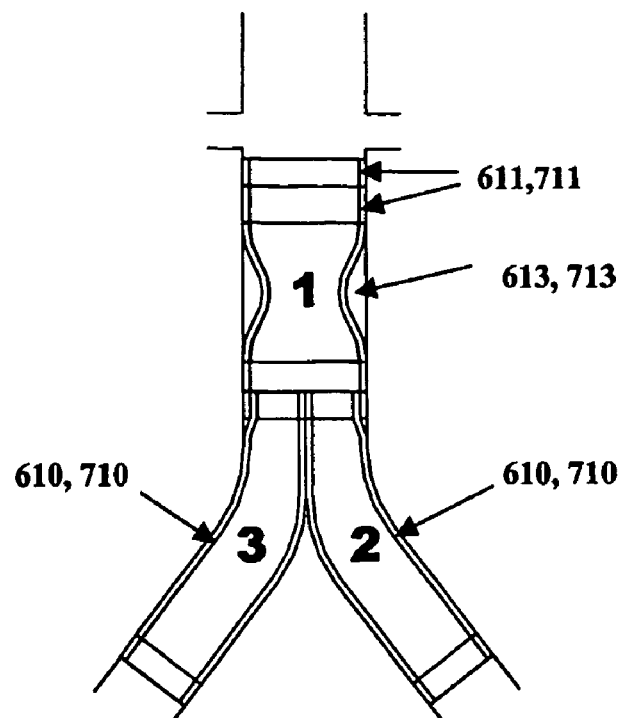
FIG. 24 illustrates a schematic of a AAA stent graft, which is formed from three devices.

Illustrated in FIG. 24 is a AAA stent graft having a combination of three devices 610 or 710. The first device labeled 1 is located in the abdominal aorta with the section 611 or 711 providing ingrowth fixing zones, and preventing migration of the device. The sections 613 and 713 provide longitudinal and circumferential compliance, as well as radial compliance.

The second and third devices labeled 2 and 3 are located in the bifurcation. The devices 2 and 3 can include compliance as in the device 1, but only if the patient's requirements dictate this.

Two Device AAA Stent Graft

Figure 25:
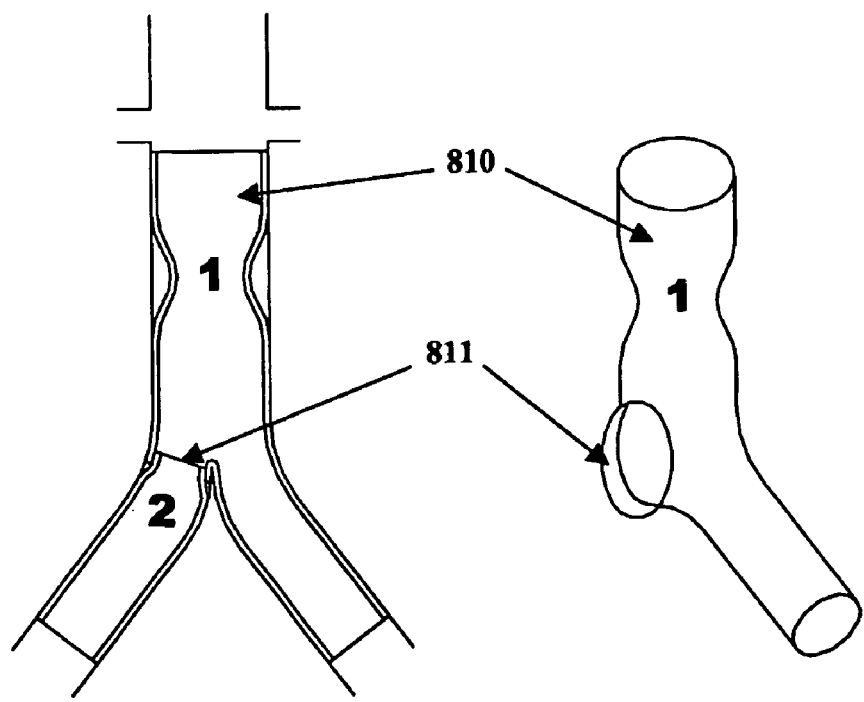
FIG. 25 illustrates a schematic of a AAA stent graft which is formed from two devices.

In FIG. 25 a two device AAA stent graft is produced. The first device 810 is a composite device where the branch for the abdominal aorta and the first branch of the bifurcation are fabricated as a single stent graft. Intermediate the ends of the device 810 is an aperture 811, which will align with the portal leading from the second branch of the bifurcation. The device 1 is located in the abdominal aorta and one branch of the bifurcation. The second device 2, such as a device 610, is then positioned into the second branch of the bifurcation with one of its ends abutting the intermediate aperture 811 in the device 1.

The stent grafts of FIGS. 24 and 25 do allow for endovascular deployment.

Bifurcated Stent Graft 910

Figure 26:
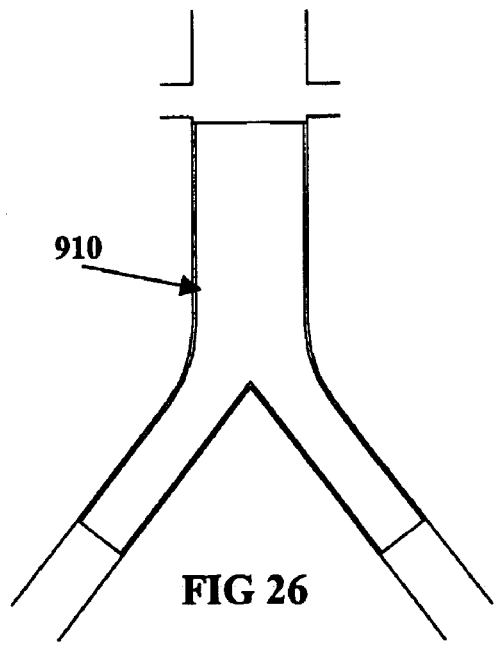
FIG. 26 illustrates a schematic of a AAA stent graft which is formed from a single device.

Illustrated in FIG. 26 is a single piece stent graft 910 being a bifurcated stent graft having a main branch and two branches downstream from the bifurcation. The device 910 can have compliant sections in its main branch and in each of its legs, if desired can have a compliant stent graft located inside, in a manner similar to that of FIG. 23.

Stent Strut Arrangements

Figure 28:
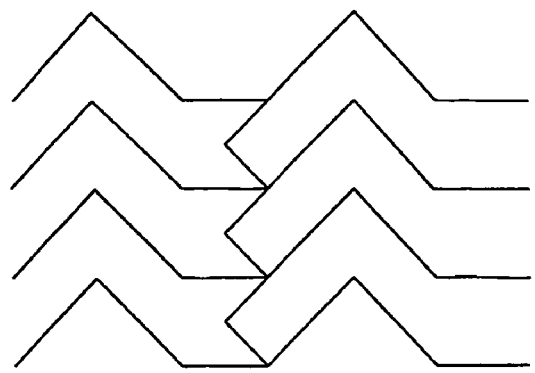
FIG. 28 illustrates a schematic of another strap or strut arrangement which could be used with the devices of the other Figures.
Figure 27:
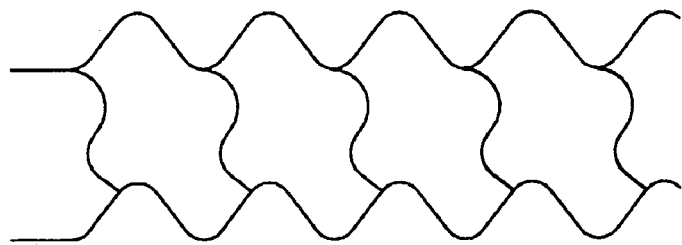
FIG. 27 illustrates a schematic of a strap or strut arrangement which could be used with the devices of the other Figures.

Illustrated in FIGS. 27 and 28 are two strut designs which could be readily useable with all the devices described above. These designs are expected to allow compliance in the radial, axial and circumferential directions of the devices made with these strut systems. Such designs could also be in the form of fibres encased within or around an elastomer material.

The above described stent-graft, graft, or stent as described with relation to FIGS. 24 and 25 can be used to address a group of second problems such as: Athero(artero)-sclerosis; plaques(stiffness & blockages), and aneurysms (reduced load bearing, rupture). The designs of the devices used in FIGS. 24, 25 and 26 can be made for AAA applications where a compliant section is deployed in the abdominal aorta and fitted with 2 endolegs (3 piece device) or made so that the abdominal section extends into the right or left endoleg portion, with a separate endoleg fitted into the remaining side. Both systems of FIGS. 24 and 25 have endoleg attachment designs that allow for sealing and joining to the other segments.

All devices described above have the possibility to be removed by possible interventional techniques. This possibility is dependent upon the use of separate sealing and attachment sections on the devices. Interventional or intraluminal endoscopic instruments may be used to react and if necessary separate vessel wall from adhesion zones in the devices.

Combined Standard Graft and Compliant Stent Graft 900

Figure 32:
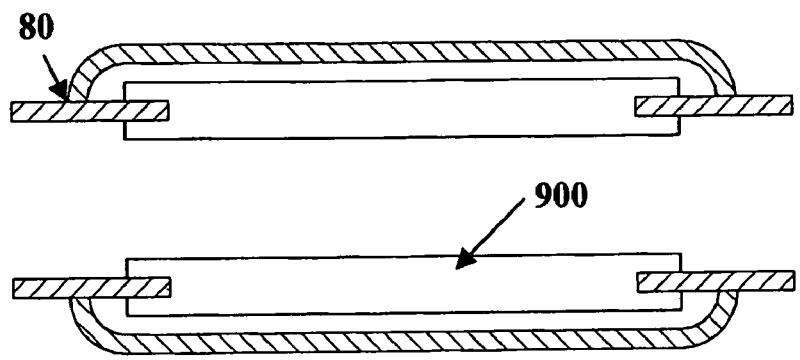
FIG. 32 illustrates a schematic cross section through a combined standard graft and compliant stent graft with a different deployment modus compared with that of FIGS. 30 and 31.

Illustrated in FIG. 32 is a combined standard graft and compliant stent graft 900 which is deployed within a vessel 80 by intraluminal or endoluminal means or by surgical means. The combined graft and stent 900 carries the load for the existing tissue for the period of time that the biodegradable substance of which it is made remains able to bear the load. This allows the regeneration of the native vessel wall around the device 900 and as the biodegradable material may include growth or other stimulation factors, it will assist with the stimulation of such regeneration.

In the devices described above and the stent graft, where the wall characteristics are such that they do not have uniform material properties through the cross section of the material, then the ratio of inner to outer wall stress of the device or graft will assist in modelling the native visco-elastic response of the vessel wall.

Compliant By-Pass Shunt 950

Figure 33:
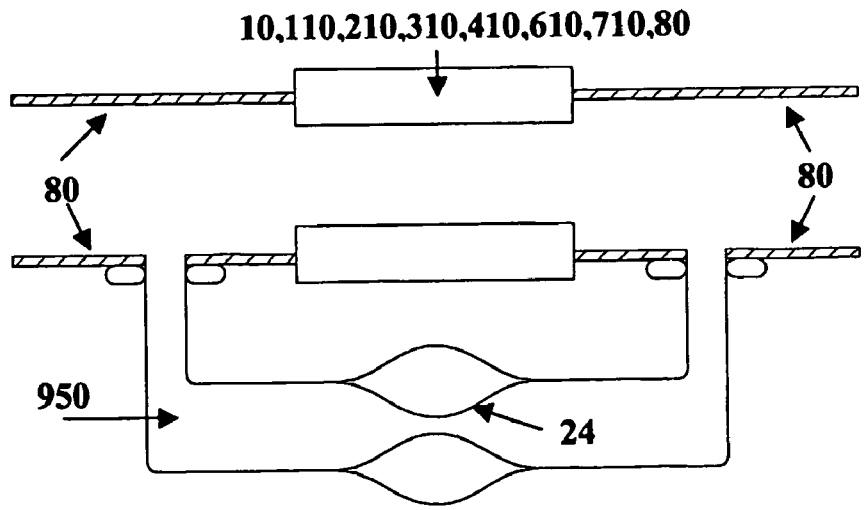
FIG. 33 illustrates a schematic cross section through a shunt by-pass including a compliance device of previous Figures in combination with a vessel or a graft or a device of the previous Figures on the main vessel.

The use of a compliant by-pass shunt 950 as shown in FIG. 33 may also provide increased compliance when desired. Adding a compliant inflatable pillow 24, as described above to a shunt 950 is like adding a capacitive component to the arterial system, which will add as much capacitance as is contained in that segment. The shunt by-pass 950 is like adding a capacitive component in parallel, and is therefore a potentially attractive approach. Such a shunt 950 can encompass any combination of the designs described. Also worth noting is that while the drawings show a compliant section with a section with a decreased diameter, adding clinical benefit may be possible by an increase in luminal cross sectional area, i.e. an increase in diameter. As such a device with up to 30% or a possibly greater increase in diameter may be used.

Adding compliant and resistance elements within a wall and or in combination with shunts, is likely to allow a greater range of performance to be achieved.

Finally, the pillow system described above can be used to provide a valve prosthesis so as to address a third group of problems such as: pressure regulation, regurgitation, heart valve problems, incontinence, and intestinal disorders. Using a pillow design as shown FIG. 33, opening and closing of the lumen using an inflation system is possible.

While this third group of problems is perhaps of a minor focus they are worthy of mention. It needs to be borne in mind that valves are a resistance or restrictive component mostly, and not a capacitive component (plus resistive) as in the compliant devices described above.

In respect of the above described embodiments, a chemical agent might be added to shrink or constrict bio-polymers in the devices described above prior to deployment. The above described technology can also be applied to other associated medical applications including but not limited to: coronary bypass grafting prostheses (in exclusion or inclusion of all grafting (vein, xeno, synthetic, biodegradable, tissue engineered substitutes); stenting applications; dialysis; others.

The embodiments described above serve to enhance the secondary heart pump action of the cardiovascular system. They have a time dependent pressure dampening effect during systole, and a time dependent pressure discharge during diastole, thus a counter pulsation enhancement, lower heart work load and enhancing blood flow during diastole, increasing aortic and coronary artery blood flow.

The systems can be particularly useful for the treatment of hypertension, and various stages of heart failure from mild to severe, and where indicated for the treatment aortic aneurysms, and for the unloading of a vessel or luminal passage. Where the device described above is interventional, such devices may be used in conjunction with a valve either attached or adjacent to a treatment site. This can be particularly relevant when the treatment site is the ascending aorta, when it may be used in conjunction with an aortic valve.

These embodiments improve the prior art by: increasing efficiency; being self-powered; being less complex, being more reliable, and highly cost effective, by comparison to prior art systems.

It will be understood that the invention disclosed and defined herein extends to al alternative combinations of two or more of the individual features mentioned or evident from the text or drawings. All of these different combinations constitute various alternative aspects of the invention.

The foregoing describes embodiments of the present invention and modifications, obvious to those skilled in the art can be made thereto, without departing from the scope of the present invention.

The invention claimed is:

1. A method of treating a vessel in a human or animal body, said method including the steps of:
preparing a patient;
identifying a site in said vessel requiring treatment for time dependent pressure dampening or diastolic time dependent pressure discharge;
positioning an implantable device against a portion of wall of said vessel at said site, whereby load applied to said vessel is borne by said wall and said implantable device, said vessel being assisted by said implantable device when said wall and said implantable device act upon said load, said implantable device including an energy storage device which is charged by said load being applied to said vessel, the energy storage device being charged with a charge selected from the group of a pressure charge and an energy charge; said implantable device operating as a closed system; and
positioning said energy storage device extraluminally with respect to said vessel.

2. A method as claimed in claim 1, wherein said charge is an energy charge which is at least in part produced by elastic deformation of said device.

3. A method as claimed in claim 1, wherein said energy storage device releases said charge to enable said implantable device to assist said wall when said wall acts upon said load.

4. A method as claimed in claim 3, wherein said energy storage device releases said charge in response to unloading of said vessel.

5. A method as claimed in claim 1, wherein said implantable device includes at least one elastomeric component, said elastomeric component being adapted to release energy to assist said vessel.

6. A method as claimed in claim 1, wherein said method includes positioning a cuff, which is a part of said implantable device, around said vessel positioned to reduce the diameter and therefore the stress-strain profile of the vessel to operate in a less stiff and more compliant manner over a physiological range of loads.

7. A method as claimed in claim 1, wherein said energy storage device is a deformable reservoir.

8. A method as claimed in claim 1, wherein said energy storage device includes a compressible media chamber which when compressed stores said charge.

9. A method as claimed in claim 8, wherein said energy storage device includes a non-compressible media chamber having communicable passage with a compressible media chamber.

10. A method as claimed in claim 1, wherein the compliance of said device is modifiable at the time of implant by inflation.

11. A method as claimed in claim 10, wherein compliance is modified by inflation with at least one of the following media: a bio-compatible fluid; liquid silicone; liquid saline; a liquid containing a contrast agent (x-ray viewable); a gel solution that expands with temperature to a final operating volume at 37° degrees Celsius; uncured polymer which thermoset at 37° C., liquid polymer which thermoset, at 37°, polymer which thermoset via activation by light, uncured polymer which thermosets by heat; a heat activated gel; elastin; collagen; elastin and collagen in combination; air; gas; a polymer that cures after injecting gas, carbon dioxide, helium, or air; a polymer that thermoses after injecting gas, carbon dioxide, helium, or air; and other compressible media.

12. A method as claimed in claim 1, wherein said vessel is a blood vessel.

13. A method as claimed in claim 1, wherein said load applied to said vessel being borne by said wall and said implantable device, thereby charging said implantable device, is in the systolic phase of a cardiovascular system.

14. A method as claimed in claim 1, wherein said implantable device discharges energy acting on said vessel in the diastolic phase of a cardiovascular system.

15. A method as claimed in claim 1, wherein said implantable device is positioned between cut ends of said vessel to replace said site.

16. A method as claimed in claim 1, wherein the compliance of said vessel is modifiable at the time of implant by inflation of said device.

17. The method of claim 1, wherein charges imparted to the energy storage device are provided exclusively by the load being applied to said vessel.

18. The method of claim 1, wherein the implantable device operates as a completely passive device.

19. The method of claim 1, wherein compliance of the implantable device is modifiable after implantation by adjusting an inflation pressure thereof.

20. The method of claim 1, wherein compliance of the vessel is modifiable after implantation of the implantable device by adjusting an inflation pressure of the implantable device.

21. The method of claim 1, wherein the vessel is the aorta.

22. The method of claim 1, wherein the implantable device is positioned over a treatment site where a part of the vessel has been removed.

23. A treatment device for operating with a wall of a vessel in a body, said treatment device including a changeable volume portion which is adapted to interact with said vessel so as to modify the volume of said vessel; and an energy storage device functioning with said changeable volume portion whereby a decrease in the volume of said changeable volume portion creates a charge in said energy storage device, said charge being able to be subsequently released to cause said changeable volume portion to increase in volume, said energy storage device being extraluminal with respect to said vessel, said energy storage device absorbing energy when loaded, and releasing energy when unloaded.

24. A device as claimed in claim 23, wherein said changeable volume portion is a cuff member which includes an inflatable portion, said cuff member and said inflatable portion being able to be positioned around said vessel, or a portion of said vessel, said device shaped to fit said vessel curvature at said vessel treatment site.

25. A device as claimed in claim 24, wherein said cuff contains said changeable volume portion and said energy storage device.

26. A device as claimed in claim 25, wherein said energy storage device is a compressible media chamber which is compressed or loaded by said vessel cuff inner portion, changing it's changeable media volume portion by compressing the chamber's media in a manner proportional to said applied load at said vessel treatment site, thereby absorbing part of said applied load, dampening said applied load and charging said device, said device releasing its charge when applied load is reduced.

27. A device as claimed in claim 23, wherein said energy storage device is a pressure storage device such as a deformable reservoir.

28. A device as claimed in claim 23, wherein said changeable volume portion is constructed at least in part from an elastomeric material, said elastomeric material being said energy storage device.

29. A device as claimed in claim 23, wherein said changeable volume portion is selected from the group including, a graft, a stent graft, a part of a stent, and a part of a stent graft.

30. A device as claimed in claim 23, wherein said changeable volume portion and said energy storage device are primed with a threshold or reference pressure.

31. A device as claimed in claim 23, wherein said changeable volume portion is primed with at least one of the following media: a bio-compatible fluid; liquid silicone ; liquid saline; a liquid containing a contrast agent which is x-ray viewable; a gel that expands with temperature to a final operating volume at 37° degrees Celsius, other solution that expands with temperature to a final operating volume at 37° degrees Celsius; elastin; collagen ; elastin and collagen in combination; air; carbon dioxide; helium; and a gas.

32. A device as claimed in claim 23, wherein said energy storage device includes a compressible media chamber.

33. A device as claimed in claim 32, wherein media with which said energy storage device is primed is at least one of the following compressible media: air; carbon dioxide, helium, and gas.

34. A device as claimed in claim 23, wherein said changeable volume portion includes a generally inextensible outer portion whereby any change of volume is confined to being within the volume defined by said outer portion.

35. A device as claimed in claim 34, wherein said energy storage device is a compressible media chamber which when compressed or loaded, absorbs part of said charge, and a non-compressible media chamber having communicable passage with said vessel cuff, said vessel cuff inner portion changing it's changeable volume portion by transfer of fluid to said non-compressible media chamber, said non-compressible media chamber acting on said compressible media chamber in a manner proportional to said applied load at said vessel treatment site.

36. A device as claimed in claim 23, wherein said changeable volume portion is joined to ends of said vessel.

37. A device as claimed in claim 23, wherein said device is used to treat a blood carrying vessel.

38. A device as claimed in claim 37, wherein said treatment device is used to repair the compliance of a portion of said vessel.

39. A device as claimed in claim 37, wherein said treatment device is used to modify the systolic and diastolic characteristics of said vessel to thereby improve cardiovascular performance.

40. A device as claimed in claim 23, wherein said device is used to treat a blood carrying vessel graft prosthesis.

41. The device of claim 23, wherein the changeable volume portion and energy storage device operate as a closed system.

42. The device of claim 23, wherein charges imparted to the energy storage device are provided exclusively via the changeable volume portion.

43. The device of claim 23, wherein the treatment device operates as a completely passive device.

* * * * *